(12) United States Patent
Hölscher et al.

(10) Patent No.: US 6,365,736 B1
(45) Date of Patent: Apr. 2, 2002

(54) BENZOXAZINE AND BENZOTHIAZINE DERIVATIVES AND THEIR USE IN PHARMACEUTICALS

(75) Inventors: Peter Hölscher; Hartmut Rehwinkel; Stefan Jaroch; Detlev Suelzle, all of Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/581,119

(22) PCT Filed: Sep. 8, 1998

(86) PCT No.: PCT/DE98/02690

§ 371 Date: Jun. 15, 2000

§ 102(e) Date: Jun. 15, 2000

(87) PCT Pub. No.: WO99/12915

PCT Pub. Date: Mar. 18, 1999

(30) Foreign Application Priority Data

Sep. 8, 1997 (DE) .......................................... 197 40 386
Jun. 5, 1998 (DE) .......................................... 198 26 232

(51) Int. Cl.$^7$ ................... C07D 265/36; C07D 213/00; C07D 333/02; A61K 31/538; A61K 31/435

(52) U.S. Cl. ................... 544/1; 544/105; 546/1; 549/29; 549/229; 549/212; 514/231.5; 514/438; 514/277; 514/461; 514/469

(58) Field of Search ............... 514/438, 231.5, 514/277, 461, 469; 544/105, 1; 546/1; 549/29, 229, 212

(56) References Cited

FOREIGN PATENT DOCUMENTS

WO    96 14844    5/1996

OTHER PUBLICATIONS

Indian J. Chem."Antiinflammatory agents",Shridar at el., Sect.B,25B/9,986–8, 1986.*

* cited by examiner

Primary Examiner—Richard L. Raymond
Assistant Examiner—Sudhaker B. Patel
(74) Attorney, Agent, or Firm—Millen, White, Zelano & Branigan, P.C.

(57) ABSTRACT

Described are benzoxazine and benzothiazine compounds of the formula I defined herein, methods for their preparation and methods for their use in pharmaceuticals based on their activity as NO-synthases (NOS) inhibitors.

15 Claims, No Drawings

BENZOXAZINE AND BENZOTHIAZINE DERIVATIVES AND THEIR USE IN PHARMACEUTICALS

The invention relates to benzoxazine and benzothiazine derivatives, the process for their production and their use in pharmaceutical agents.

In human cells, there exist 3 specific forms of nitrogen monoxide synthases, which convert arginine into nitrogen monoxide (NO) and citrulline. Two constitutive NO-synthases (NOS) were identified that are present as $Ca^{++}$/calmodulin-dependent enzymes in the brain (ncNOS or NOS 1) or in the endothelium (ecNOS or NOS 3). The third isoform is the inducible NOS (iNOS or NOS 2), which is a $Ca^{++}$-independent enzyme and is induced after activation of different cells by endotoxin.

NOS-inhibitors and especially specific inhibitors of NOS 1, NOS 2 or NOS 3 are therefore suitable for treatment of different diseases, which are induced or aggravated by pathological concentrations of NO in cells (Clin. Neuropharmac. 18, 1995, page 482).

As NOS-inhibitors, different compounds are known. For example, cyclic amidine derivatives are described in WO 96/14844. It is not known from any publication, however, that benzoxazines or benzothiazines inhibit nitrogen monoxide synthases.

The invention relates to the compounds of Formula I, their tautomeric and isomeric forms and salts

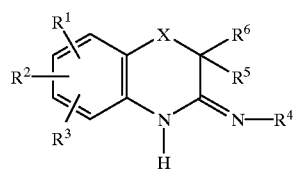

(I)

in which

X means O, $SO_m$ or Se, $R^1$ means $NO_2$, cyano, $CF_3$, $-OCF_3$, $-SO_2NR^7R^8$, $-CONR^7R^8$, $-NR^9-C(=NR^{10})-R^{11}$, $-NH-CS-NR^7R^8$, $-NH-CO-NR^7R^8$, $NR^{12}R^{13}$, $-CO-R^{14}$, $C_{6-10}$ aryl, which optionally is substituted with halogen, cyano $C_{1-4}$ alkyl, $-S-R^9$, $-O-R^9$, $-NR^7R^8$ or $CONR^7R^8$, 5- or 6-membered heteroaryl with 1 to 4 heteroatoms, such as oxygen, nitrogen or sulfur, which optionally is substituted with $-OR^9$, $-SR^9$, halogen, $C_{1-4}$ alkyl, $NR^7R^8$ or $CONR^7R^8$, $C_{1-6}$ alkyl, which is substituted with halogen, $-OR^9$, $-SR^9$, $-NR^7R^8$, $-NR^7R^{8'}$, $=NR^7$, $=NOC_{1-6}$ alkyl, $=N-NHaryl$, phenyl, $C_{3-7}$ cycloalkyl or 5- or 6-membered heteroaryl, with 1–3 N, O, or S atoms, $C_{2-6}$ alkenyl, which is substituted with halogen, $CONH_2$, $C\equiv N$ or phenyl, $C_{2-6}$ alkinyl, which is substituted with halogen, $CONH_2$, $C\equiv N$ or phenyl, $C_{3-7}$ cycloalkyl, $R^2$ means hydrogen or $R^1$ and $R^2$ together with two adjacent carbon atoms form a 5-, 6-, 7- or 8-membered ring, which can be monocyclic or bicyclic, saturated or unsaturated and in which 1 or 2 $CH_2$ groups can be replaced by oxygen or carbonyl or its derivative, and which can be substituted with $-NR^7R^8$, $-NR^7R^{8'}$ or $C_{1-4}$ alkyl, $R^3$ means hydrogen, halogen, $-S-R^9$ or $-O-R^9$ or is the same or different from $R^1$, $R^4$ means hydrogen or acyl, $R^5$ means hydrogen, $R^6$ means $C_{3-7}$ cycloalkyl, $C_{6-10}$ aryl, $C_{1-6}$ alkyl, $C_{2-6}$ alkenyl or $C_{2-6}$ alkynyl radicals, which can be substituted in each case with halogen, OH, $O-C_{1-6}$ alkyl, SH, $S-C_{1-6}$ alkyl, $NR^{15}R^{16}$, 5- or 6-membered heteroaryl with 1–3 N, O or S atoms, phenyl or $C_{3-7}$ cycloalkyl, $R^7$ and $R^8$ mean hydrogen, $C_{1-6}$ alkyl, phenyl optionally substituted with halogen or $C_{1-4}$ alkyl, benzyl optionally substituted with halogen or $C_{1-4}$ alkyl or $C_{3-7}$ cycloalkyl, $R^{7'}$ means hydrogen, $C_{1-6}$ alkyl optionally substituted with OH, phenyl, cyano, $COO_{1-4}$ alkyl or carbonyl, $R^{8'}$ means $C_{1-6}$ alkyl, which is substituted with $C_{3-7}$ cycloalkyl, indanyl, $C_{6-10}$ aryl or 5- or 6-membered heteroaryl with 1–3 nitrogen, oxygen or sulfur atoms, whereby the aryl and heteroaryl radicals can be substituted with halogen, $C_{1-4}$ alkyl, $C_{1-4}$ alkoxy, $CF_3$, $NO_2$, $NH_2$, $N(C_{1-4}$ alkyl$)_2$, $SO_2CH_3$, $-O-CH_2-O$, $SO_2NH_2$, OH or $COO-C_{1-4}$ alkyl, or indanyl or 1,2,3,4-tetrahydronaphthyl or $R^{7'}$ and $R^{8'}$ together with the nitrogen atom form a 5- to 7-membered saturated heterocycle, which can contain another oxygen, nitrogen or sulfur atom and can be substituted with $C_{1-4}$ alkyl, phenyl, benzyl or benzoyl or form an unsaturated 5-membered heterocycle, which can contain 1–3 N atoms and can be substituted with phenyl, $C_{1-4}$ alkyl, halogen or $CH_2-OH$, $R^9$, $R^{10}$ and $R^{15}$, $R^{16}$ mean hydrogen or $C_{1-6}$ alkyl, $R^{11}$ means $C_{1-6}$ alkyl, $-NH_2$, $-NH-CH_3$, $-NH-CN$, $C_{6-10}$ aryl optionally substituted with halogen, $C_{1-4}$ alkyl or $CF_3$, or 5- or 6-membered heteroaryl with 1 to 4 nitrogen, sulfur or oxygen atoms that optionally is substituted with halogen, $C_{1-4}$ alkyl or $CF_3$, m means 0, 1 or 2, $R^{12}$, $R^{13}$ together with the nitrogen atom form a saturated 5-, 6- or 7-membered ring, which can contain another nitrogen, oxygen or sulfur atom and can be substituted with $C_{1-4}$ alkyl, phenyl, benzyl or benzoyl and $R^{14}$ means hydrogen, phenyl, $C_{1-6}$ alkyl optionally substituted with $CO_2H$, $CO_2C_{1-6}$ alkyl, hydroxy, $C_{1-4}$ alkoxy, halogen, $NR^7R^8$, $NR^{12}R^{13}$, $CONR^7R^8$ or phenyl, or $C_{2-6}$ alkenyl optionally substituted with phenyl, cyano, $CONR^7R^8$ or $CO_2C_{1-4}$ alkyl.

The compounds of the formula can be present as tautomers, stereoisomers or geometric isomers. The invention also comprises all possible isomers, such as E- and Z-isomers, S- and R-enantiomers, diastereomers, racemates and mixtures thereof, including the tautomeric compounds of Formulas 1a and 1b

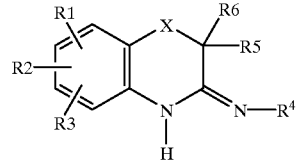

Ia

-continued

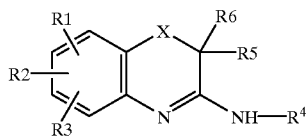

Ib

The physiologically compatible salts can be formed with inorganic and organic acids, such as, for example, oxalic acid, lactic acid, citric acid, fumaric acid, acetic acid, maleic acid, tartaric acid, phosphoric acid, HCl, HBr, sulfuric acid, p-toluenesulfonic acid, methanesulfonic acid, i.a.

For salt formation of acid groups, the inorganic or organic bases are also suitable, which are known for the formation of physiologically compatible salts, such as, for example, alkali hydroxides, such as sodium and potassium hydroxide, alkaline-earth hydroxides, such as calcium hydroxide, ammonia, amines such as ethanolamine, diethanolamine, triethanolamine, N-methylglucamine, tris-(hydroxymethyl)-methylamine, etc.

In each case, alkyl means a straight-chain or branched alkyl group, such as, e.g., methyl, ethyl, propyl, isopropyl, n-butyl, sec-butyl, tert-butyl, n-pentyl, sec-pentyl, tert-pentyl, neopentyl, n-hexyl, sec-hexyl, heptyl, octyl, especially $C_{1-4}$ alkyl groups.

Alkenyl and alkynyl substituents are in each case straight-chain or branched. For example, the following radicals can be mentioned: vinyl, 2-propenyl, 1-propenyl, 2-butenyl, 1-butenyl, 1-butenyl, 2-butenyl, 1-methyl-1-propenyl, 2-methyl-2-propenyl, 3-methyl-2-propenyl, ethinyl, 1-propinyl, 2-propinyl, 1-butinyl, 2-butinyl.

Cycloalkyl is defined respectively as cyclopropyl, cyclobutyl, cyclopentyl, cyclohexyl or cycloheptyl.

Halogen means respectively fluorine, chlorine, bromine or iodine.

Aryl is defined respectively as naphthyl or phenyl, which can be substituted in one or more places. Phenyl and benzyl radicals $R^7$, $R^8$ and $R^{8'}$ can also be substituted by the same or a different component in one or more places at any position.

The hetaryl radical can contain a fused benzene ring in each case and can be substituted by the same or a different component in one to three places and can be bonded via the heteroatom or a carbon atom. For example, the following 5- and 6-ring heteroaromatic compounds are suitable in each case:

Imidazole, indole, isooxazole, isothiazole, furan, oxadiazole, oxazole, pyrazine, pyridazine, pyrimidine, pyridine, pyrazole, pyrrole, tetrazole, thiazole, triazole, thiophene, thiadiazole, benzimidazole, benzofuran, benzoxazole, isoquinoline, quinoline. Preferably, pyridine, pyrrole, thiophene, thiazole and imidazole can be mentioned.

As a preferred embodiment for $R^{11}$ in the meaning of heteroaryl, thienyl can be considered.

As saturated heterocycles $NR^{12}R^{13}$, and $NR^7R^{8'}$, for example, piperidine, pyrrolidine, morpholine, thiomorpholine, hexahydroazepine and piperazine can be mentioned. The heterocycle can be substituted in 1 to 3 places with $C_{1-4}$ alkyl or a phenyl, benzyl or benzoyl radical that optionally is substituted with halogen. For example, there can be mentioned: N-methyl-piperazine, 2,6-dimethylmorpholine, phenylpiperazine or 4-(4-fluorobenzoyl)-piperidine.

If $NR^7R^{8'}$ together with the nitrogen atom form an unsaturated heterocycle, for example, imidazole, pyrrole, pyrazole, triazole, benzimidazole and indazole can be mentioned, which can be substituted in one to two places with phenyl, $C_{1-4}$ alkyl, halogen, especially chlorine or $CH_2$—OH.

Alkyl radical $R^{8'}$ can be substituted by the same or a different component in one or two places. If the substituent of alkyl radical $R^{8'}$ means a heteroaryl radical, the heteroaryl radicals that are mentioned for $R^{11}$ are suitable, but cannot be linked via an N atom.

If $R^{8'}$ means indanyl or 1,2,3,4-tetrahydronaphthyl, this radical can be linked in each case in 1- or 2-position.

Substituent $R^6$ preferably means alkyl, which can be substituted and especially $C_{1-6}$ alkyl.

If $R^1$ and $R^2$ together with two adjacent carbon atoms form a 5-, 6-, 7- or 8-membered ring, the latter can be in 5,6- or 6,7- or 7,8-position of the benzoxazine or benzothiazine and has formula

in which

A means a saturated or unsaturated $C_{3-8}$ alkylene radical, which can be substituted with $-NR^7R^8$, $-NR^7R^{8'}$ or $C_{1-4}$ alkyl by the same or a different component in 1 to 4 places and in which 1 or 2 $CH_2$ groups can be replaced by oxygen or carbonyl or its derivative, and whereby the alkylene radical can contain a slightly condensed benzene radical, such as, for example, indan, or can be present as a bicyclic compound, such as, for example, bicycloheptane.

As structures of A, there can be mentioned, for example;

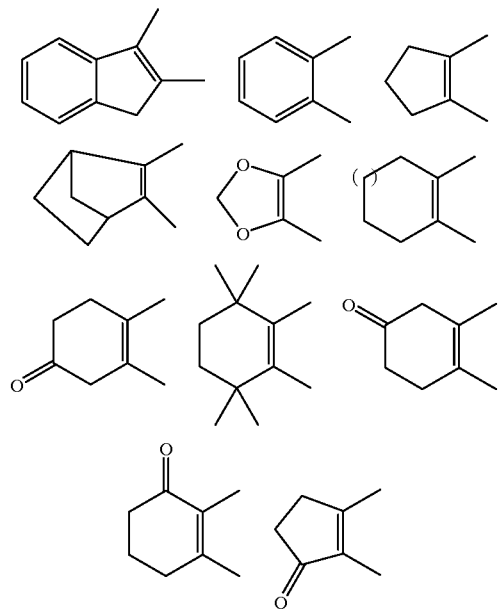

As carbonyl derivatives, for example, $=NOH$, $=N-OC_{1-6}$ alkyl, $=NH-NH_2$, $=N-NH$-phenyl are suitable. Preferably, two adjacent carbon atoms of the aromatic compound are linked with $C_{1-6}$ alkylene to a 3- to 8-membered unsaturated ring, which can be substituted in any position.

Acyl radical $R^4$ is derived from especially straight-chain or branched $C_{1-6}$ aliphatic carboxylic acids, such as, for example, formic acid, acetic acid, propionic acid, butyric acid, trimethylacetic acid or caproic acid or from known benzenesulfonic acids, which can be substituted with halogen or $C_{1-4}$ alkyl, and $C_{1-4}$ alkanesulfonic acids suitable, such as, for example, methanesulfonic acid, p-toluenesulfonic acid.

Preferred embodiments of X are S and O, and a preferred embodiment of $R^3$ is hydrogen.

$R^4$ preferably means hydrogen.

The invention also relates to the use of the compounds according to the invention for the production of a pharmaceutical agent for treating diseases, which are induced by the action of nitrogen monoxide at pathological concentrations. These include neurodegenerative diseases, inflammatory diseases, auto-immune diseases, and cardiovascular diseases.

For example, there can be mentioned: cerebral ischemia, hypoxia and other neurodegenerative diseases, which are brought into contact with inflammations, such as multiple sclerosis, amyotrophic lateral sclerosis and comparable sclerotic diseases, Parkinson's Disease, Huntington's Disease, Korksakoff's Disease, epilepsy, vomiting, stress, sleep disorders, schizophrenia, depression, migraine, hypoglycemia, dementia, such as, e.g., Alzheimer's Disease, HIV-dementia and presenile dementia.

They are also suitable for treating diseases of the cardiovascular system and for treating auto-immune and/or inflammatory diseases, such as hypotension, ARDS (adult respiratory distress syndrome), sepsis or septic shock, rheumatoid arthritis, osteoarthritis, insulin-dependent diabetes mellitus (IDDM), inflammatory disease of the pelvis/intestine (bowel disease), meningitis, glomerulonephritis, acute and chronic liver diseases, diseases by rejection (for example allogenic heart, kidney or liver transplants) or inflammatory skin diseases such as psoriasis, etc. Based on their profile of action, the compounds according to the invention are very well suited for inhibiting the neuronal NOS.

To use the compounds according to the invention as pharmaceutical agents, they are brought into the form of a pharmaceutical preparation, which in addition to the active ingredient contains vehicles, adjuvants and/or additives that are suitable for enteral or parenteral administration. The administration can be done orally or sublingually as a solid in the form of capsules or tablets or as a liquid in the form of solutions, suspensions, elixirs, aerosols or emulsions or rectally in the form of suppositories or in the form of injection solutions that can also optionally be used subcutaneously, intramuscularly or intravenously, or topically or intrathecally. As adjuvants for the desired pharmaceutical agent formulation, the inert organic and inorganic support media that are known to one skilled in the art are suitable, such as, e.g., water, gelatin, gum arabic, lactose, starch, magnesium stearate, talc, plant oils, polyalkylene glycols, etc. Moreover, preservatives, stabilizers, wetting agents, emulsifiers or salts for changing the osmotic pressure or buffers can optionally be contained.

For parenteral administration, especially injection solutions or suspensions, especially aqueous solutions of the active compounds in polyhydroxyethylated castor oil, are suitable.

As vehicle systems, surface-active adjuvants such as salts of bile acids or animal or plant phospholipids, but also mixtures thereof as well as liposomes or their components can be used.

For oral administration, especially tablets, coated tablets or capsules with talc and/or hydrocarbon vehicles or binders, such as, for example, lactose, corn or potato starch, are suitable. The administration can also be done in liquid form, such as, for example, as a juice, to which optionally a sweetener is added.

The dosage of the active ingredient can vary depending on method of administration, age and weight of the patient, type and severity of the disease that is to be treated and similar factors. The daily dose is 1–2000 mg, preferably 20–500 mg, whereby the dose can be given as an individual dose to be administered one time or divided into 2 or more daily doses.

The NOS-inhibitory action of the compounds of Formula I and their physiologically compatible salts can be determined according to the methods by Bredt and Snyder in Proc. Natl. Acad. Sci. USA (1989) 86, 9030–9033.

The production of the compounds according to the invention is carried out in that a compound of formula II or its salt

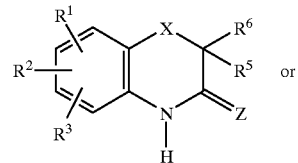

IIa

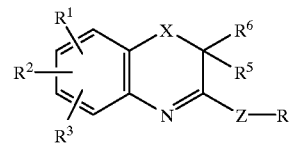

IIb in which
$R^1$, $R^2$, $R^3$, $R^5$, $R^6$ and X have the above-mentioned meaning, Z is oxygen or sulfur and R means $C_{1-6}$ alkyl, is reacted with ammonia or primary or secondary amines, whereby existing primary and secondary amino groups are optionally intermediately protected and optionally then acylated, the isomers are separated or the salts are formed.

The reaction with ammonia is possible under pressure in autoclaves with excess ammonia at low temperatures (−78° C.) or by stirring in methanol that is saturated with ammonia at room temperature. Thiolactams are preferably reacted. If the reaction is with amines, first the iminoethers or iminothioethers are produced from lactam or thiolactam as intermediate compounds (e.g., with methyl iodide or methyl sulfate), and the latter are reacted with or without isolation of the intermediate compounds with the corresponding amines or their salts.

As amino protective groups, for example, carbamates, such as tert-butoxycarbonyl, benzyloxycarbonyl or acetyl, are suitable.

In the precursor stages, optionally sulfides are oxidized, esters are saponified, acids are esterified, hydroxy groups are etherified or acylated, amines are acylated, alkylated, diazotized, halogenated, $NO_2$ is introduced or reduced, reacted with isocyanates or isothiocyanates, the isomers are separated or the salts are formed.

The saponification of an ester group can be done basically or acidically by hydrolysis being performed at room temperature or at an elevated temperature up to boiling temperature of the reaction mixture in the presence of alkali hydroxides in ethanol or other alcohols or with use of acids, such as, e.g., hydrochloric acid, and optionally salts of aminobenzoxazines or -thiazines being further processed.

The esterification of carboxylic acid is done in a way that is known in the art with diazomethane or the corresponding alcohol in acid or in the presence of an activated acid derivative. As activated acid derivatives, for example, acid chloride, acid imidazolide or acid anhydride are suitable.

The reduction of an ester group to alcohol is carried out in a way that is known in the art with DiBAH in suitable solvents at low temperatures. The reductive amination of benzaldehyde with amine while adding boron hydride provides benzylic amines.

In addition, a nitro group or halogen, especially bromine, can be introduced by electrophilic, aromatic substitution. Mixtures that are produced in this case can be separated in the usual way, also using HPLC. If a nitrile is present, the latter can be saponified according to known processes or can be converted into the corresponding amine, tetrazole or amidoxime, or it is converted into a substituted amidine by attacking substituted anilines or amines.

The Friedel-Crafts acylation is used successfully in lactams of type IIa, and then the lactam can be converted selectively into the thiolactam.

The reduction of the nitro group or optionally the cyano group to the amino group is carried out catalytically in polar solvents at room temperature or at an elevated temperature under hydrogen pressure. As catalysts, metals such as Raney nickel or noble metal catalysts such as palladium or platinum optionally in the presence of barium sulfate or on vehicles are suitable. Instead of hydrogen, ammonium formate or formic acid can also be used in a known way. Reducing agents such as tin(II) chloride or titanium(III) chloride can also be used, such as complex metal hydrides optionally in the presence of heavy metal salts. The ester group can be advantageously introduced before the reduction. For nitro groups, the reduction with zinc or iron in acetic acid has proven its value.

If a single or multiple alkylation of an amino group or a CH-acid carbon position is desired, alkylation can be performed with, for example, alkyl halides according to commonly used methods. Protection of the lactam group as an anion by a second equivalent base or by a suitable protective group optionally is necessary.

The acylation of the amino group is carried out in the usual way with, for example, an acid halide or acid anhydride, optionally in the presence of a base.

The introduction of the halogens chlorine, bromine or iodine via the amino group can also be carried out, for example, according to Sandmeyer, by the diazonium salts that are formed intermediately with nitrites being reacted with Cu(I) chloride or Cu(I) bromide in the presence of the corresponding acids such as hydrochloric acid or hydrobromic acid or being reacted with potassium iodide.

Benzyl alcohols can be converted into corresponding benzyl halides as usual with methanesulfonyl chloride.

The introduction of an $NO_2$ group is possible by a number of known nitration methods. For example, nitration can be performed with nitrates or with nitronium tetrafluoroborate in inert solvents, such as halogenated hydrocarbons or in sulfolane or glacial acetic acid. Introduction by, e.g., nitrating acid in water or concentrated sulfur acid as a solvent is also possible at temperatures of between −10° C. and 30° C.

The isomer mixtures can be separated into enantiomers or E/Z-isomers according to commonly used methods, such as, for example, crystallization, chromatography or salt formation. The enantiomers can also be obtained by chromatography on chiral phases as well as by stereoselective syntheses.

The production of the salts is carried out in the usual way, by a solution of the compound of Formula I being mixed with the equivalent amount of acid or excess acid, which optionally is in solution, and the precipitate being separated or the solution being worked up in the usual way.

If the production of the starting compounds is not described, the latter are known and commercially available or can be produced analogously to known compounds or according to processes that are described here.

Nucleophilic substitution of benzyl halides with secondary amines yields the corresponding benzylamines.

Thiolactams of Formula IIa (Z=S) are obtained from, for example, lactams with phosphorus pentasulfide ($P_4S_{10}$) or Lawesson's reagent (2,4-bis(4-methoxyphenyl)-1,3,2,4-dithiaphosphetane-2,4-disulfide) in suitable solvents, and compounds of Formula IIb can be obtained by, for example, reaction with Meerwein reagent (trimethyloxonium tetrafluoroborate).

The production of the compounds of Formula IIa can be done, for example, in that a compound of Formula III

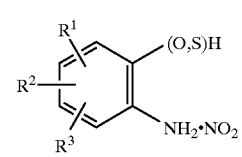

III in which $R^1$ to $R^3$ have the above-mentioned meaning, is reacted with a compound of Formula IV

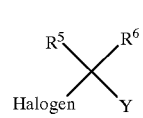

IV in which $R^5$ and $R^6$ have the above-mentioned meaning, and Y is a reactive carboxyl group such as acid halide, nitrile, carboxylic acid ester, and optionally is reductively cyclized, or in that a compound of Formula V

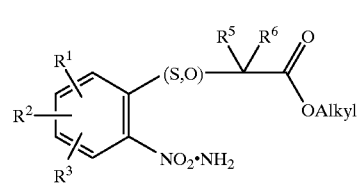

V is reductively cyclized.

Aromatic thiols of type III are obtained, i.a., as described in Chem. Pharm. Bull. 1991, 39, 2888 and the literature that is mentioned there by rearrangement of the corresponding dimethylaminothiocarbamates.

The introduction of substituents $R^1$ to $R^3$ can be carried out in the stage of the compounds of Formula III or II.

For the production of compounds of Formula II with $R^1$ in the meaning of an alkyl radical that is substituted with $NR^7R^{8'}$ or if $R^1$ and $R^2$ together mean a ring that is substituted with $NR^7R^{8'}$, the aldehyde or the ketone of the corresponding 1,4-benzoxazine-3-thione or 1,4-benzothiazine-3-thione can be reductively aminated. If the introduction of a heteroaryl radical $NR^7R^{8'}$ is desired, the corresponding halogen derivative can be substituted nucleophilically. If a primary or secondary amino group is present, it can be advantageous to protect the latter intermediately, for example by introduction of a tert-butoxycarbonyl group, which is usually cleaved according to the amidine formation.

New compounds were identified by one or more of the following methods: melting point, mass spectroscopy, infrared spectroscopy, nuclear magnetic resonance spectroscopy (NMR). NMR spectra were measured with a Bruker 300 MHz device; the (deuterated) solvents were respectively indicated and abbreviated as follows: $CDCl_3$ (chloroform), DMSO (dimethyl sulfoxide). Alterations are indicated in delta and ppm. br means broad signal; m means multiplet, several signals; s means singlet; d means doublet; dd means double doublet, etc.; tr means triplet; q means quartet; H means hydrogen protons; J means coupling constant. In addition, THF means tetrahydrofuran; DMF means N,N-dimethylformamide; MeOH means methanol; EE means ethyl acetate; ml means milliliter; RT means room temperature. All solvents are p.A. grade, unless otherwise indicated. All reactions are carried out under a cover gas, unless these are aqueous solutions. Melting points are indicated in degrees Celsius and are not corrected.

The invention also relates to the compounds of Formula IIa, in which $R^3$, $R^5$, $R^6$, X and Z have the above-described meaning, and $R^1$ and $R^2$ together with two adjacent carbon atoms form a 5-, 6-, 7- or 8-membered ring, in which A means a saturated or unsaturated $C_{3-8}$ alkylene radical, in which 1 or 2 $CH_2$ groups can be replaced by carbonyl or its derivative. They are valuable intermediate compounds for the production of pharmacologically active compounds. The conversion of intermediate products into active substances is carried out according to the above-described processes.

Below, the production of several precursors, intermediate products and products is described by way of example.

Starting Compounds (1)

A) 6-Chloro-7-nitro-2-methyl-1,4-benzoxazin-3-one 7.52 g of 2-amino-4-chloro-5-nitrophenol is added to a mixture of 1.6 g of sodium hydride in 60 ml of DMF and mixed with 1.1 equivalents of D,L-2-bromopropionic acid ethyl ester in 20 ml of THF at 5° C. It is stirred for 4 hours. The mixture is poured onto water, extracted with ethyl acetate, the organic phase is dried with magnesium sulfate and concentrated by evaporation. 1.7 g of crude product, which is recrystallized from isopropyl ether, results. The yield is 72%.

[1H]-NMR ($CDCl_3$): 10.85 br 1H, 7.55 s 1H, 7.03 s 1H, 4.60 q 1H, 1.51 d 3H.

According to the process that is mentioned here and in B), enantiomer-pure compounds can be produced, which can be used in further reactions.

The following is produced in the same way:

8-Chloro-6-nitro-2-methyl-1,4-benzoxazin-3-one

The yield is 51%. [1H]-NMR (DMSO): 11.1 br 1H, 7.98 d 1H, 7.72 d 1H, 5.05 q 1H, 1.53 d 3H.

B) 6-Phenyl-2-methyl-1,4-benzoxazin-3-one 4.5 g of 3-amino-4-hydroxybiphenyl is mixed in 34 ml of DMF with 3.5 ml of D,L-2-bromopropionic acid ethyl ester (1.1 equivalents) as well as with 4.48 g of potassium carbonate, and it is stirred at 70° C. for 5 hours. The mixture is poured onto water, extracted with ethyl acetate, the organic phase is washed, dried with magnesium sulfate and concentrated by evaporation. 1.7 g of crude product, which is recrystallized from isopropanol, results.

[1H]-NMR (DMSO): 10.65 br 1H, 7.6–7.3 m 8H, 4.72 q 1H, 1.48 d 3H.

The following are produced in the same way:

6-Benzyl-2-methyl-1,4-benzoxazin-3-one
5-nitro-2-methyl-1,4-benzoxazin-3-one
6-nitro-2-methyl-1,4-benzoxazin-3-one
7-nitro-2-methyl-1,4-benzoxazin-3-one
6-nitro-2-ethyl-1,4-benzoxazin-3-one
7-nitro-2-ethyl-1,4-benzoxazin-3-one
6-cyano-2-methyl-1,4-benzoxazin-3-one
6-trifluoromethyl-2-methyl-4-benzoxazin-3-one
9-H-fluoreno-[2,3-b]-2-methyl-1,4-oxazin-3-one from 3-amino-2-hydroxyfluorene.

1H-Naphtho [2,1-b]-3-methyl-1,4-oxazin-2-one
1H-naphth[2,1-b]-3-ethyl-1,4-oxazin-2-one from 1-aminonaphth-2-ol.

4H-Naphtho[2,3-b]-2-methyl-1,4-oxazin-3-one
4H-naphth[2,3-b]-2-ethyl-1,4-oxazin-3-one
4H-naphth[2,3-b]-2H-1,4-oxazin-3-one
4H-naphtho[2,3-b]-2-propyl-1,4-oxazin-3-one from 3-aminonaphth-2-ol.

4H-Naphtho[1,2-b]-2-methyl-1,4-oxazin-3-one
4H-naphth[1,2-b]-2-ethyl-1,4-oxazin-3-one from 2-amino-1-naphthol, which is obtained by reduction of 2-nitro-1-naphthol.

C) 6-(Imidazol-1-yl)-7-nitro-2-methyl-1,4-benzoxazin-3-one 485 mg of 6-chloro-7-nitro-2-methyl-1,4-benzoxazin-3-one is stirred with 136 mg of imidazole and 332 mg of potassium carbonate in 15 ml of DMF with the addition of copper powder for 6 hours at 180° C. It is diluted with ethyl acetate, extracted with brine, and the organic phase is dried. The crude product is purified by column chromatography with ethyl acetate with the addition of ethanol. 88 mg results.

[1H]-NMR (DMSO): 11.2 br 1H, 7.83 s br 2H, 7.38 s br 1H, 7.1 s 1H, 6.98 s 1H, 4.93 q 1H, 1.55 d 3H.

D) 5,6,7,8-Tetrahydro-3-nitro-2-naphthol and 5,6,7,8-tetrahydro-1-nitro-2-naphthol 14.8 g of 5,6,7,8-tetrahydro-2-naphthol is nitrated with 4.35 ml of fuming nitric acid in 100 ml of glacial acetic acid. The internal temperature should not exceed 10° C. in this case. After 1 hour, the mixture is poured onto ice water, extracted with dichloromethane and then with ethyl acetate, the combined organic phases are washed with water, dried and concentrated by evaporation. Column chromatography with hexane/ethyl acetate yields two regioisomers with a yield of 25% each as well as 5,6,7,8-tetrahydro-1,3-dinitro-2-napthol. The method that is mentioned in Chem. Pharm. Bull. 1991, 39, 2896 yields similar results.

The following are produced in the same way:

6-Nitro-5-indanol as well as 4-nitro-5-indanol from 5-indanol in a yield of 57% together. The compounds are alkylated together as described in Example B), cyclized as described in Example G) and only the products of this reaction are separated.

5-Hydroxy-6-nitro-benzo-1,3-dioxol is produced as described in J. Org. Chem. 1959, 24, 327.

In Eur. J. Med. Chem. Chim. Therap. 1974, 9, p. 26, the production of 6-hydroxy-1,2,3,4-tetrahydro-1,4-methanonapthalene is described, which is nitrated as indicated above. The mixture of the nitro compounds is separated by chromatography, and 5,6,7,8-tetrahydro-5,8-methano-3-nitronaphth-2-ol is obtained.

From 5,5,8,8-tetramethyl-5,6,7,8-tetrahydro-naphth-2-ol, 5,5,8,8-tetramethyl-5,6,7,8-tetrahydro-3-nitro-naphth-2-ol is obtained.

E) 6-Nitro-5-methoxy-indan-1-one 0.81 g of 5-methoxy-indan-1-one is nitrated with 1.33 g of copper(II) nitrate in 7.5 ml of acetic anhydride at room temperature. After 3 hours, it is poured onto ice water, extracted several times with ethyl acetate, the organic phase is washed with hydrogen carbonate solution, then with brine, dried and concentrated by evaporation. Column chromatography with hexane/ethyl acetate yields two regioisomers; 6-nitro-5-methoxy-indan-1-one is obtained with a yield of 38%.

[1H]-NMR (CDCl$_3$): 8.19 s 1H, 7.11 s 1H, 4.05 s 3H, 3.21 dd 2H, 2.75 dd 2H.

The following are produced in the same way:
5-Nitro-6-methoxy-indan-1-one
7-nitro-6-methoxy-2-tetralon
6-nitro-7-methoxy-2-tetralon
7-nitro-6-methoxy-1-tetralon The methoxy compounds are cleaved in a customary way with HBr or lithium chloride in DMF into the substituted hydroxyaromatic compounds.

F) 2-(5,6,7,8-Tetrahydro-3-nitro-2-naphthoxy)-propionic acid ethyl ester 5,6,7,8-Tetrahydro-3-nitro-2-naphthol is alkylated according to the general instructions that are mentioned in Example A) with D,L-2-bromopropionic acid ethyl ester. After column chromatography with hexane/ethyl acetate, the nitro compound is obtained in a yield of 43%.

[1H]-NMR (CDCl$_3$): 7.60 s 1H, 6.65 s 1H, 4.77 q 1H, 4.2 q 2H, 2.74 and 1.8 m each 4H, 1.59 d 3H, 1.25 tr 3H.

The following are produced in the same way:
2-(5,6,7,8-Tetrahydro-1-nitro-2-naphthoxy)-propionic acid ethyl ester
2-(5,6,7,8-tetrahydro-3-nitro-2-naphthoxy)-butyric acid ethyl ester
2-(5,6,7,8-tetrahydro-1-nitro-2-naphthoxy)-butyric acid ethyl ester
2-(5,6,7,8-tetrahydro-3-nitro-2-naphthoxy)-acetic acid ethyl ester
2-(5,6,7,8-tetrahydro-1-nitro-2-naphthoxy)-acetic acid ethyl ester
2-(2-nitro-4,5-methylenedioxy-phenoxy)-propionic acid ethyl ester
2-(6-nitro-5-indanoxy)-propionic acid ethyl ester and 2-(4-nitro-5-indanoxy)-propionic acid ethyl ester
2-(6-nitro-5-indanoxy)-butyric acid ethyl ester and 2-(4-nitro-5-indanoxy)-butyric acid ethyl ester
2-(6-oxo-5,6,7,8-tetrahydro-1-nitro-2-naphthoxy)-propionic acid ethyl ester
2-(7-oxo-5,6,7,8-tetrahydro-1-nitro-2-naphthoxy)-propionic acid ethyl ester
2-(8-oxo-5,6,7,8-tetrahydro-1-nitro-2-naphthoxy)-propionic acid ethyl ester
2-(5,6,7,8-tetrahydro-5,8-methano-3-nitro-2-naphthoxy)-propionic acid ethyl ester
2-(5,5,8,8-tetramethyl-5,6,7,8-tetrahydro-3-nitro-2-naphthoxy)-propionic acid ethyl ester
2-(1-keto-6-nitro-5-indanoxy)-propionic acid ethyl ester G) 2-Methyl-6,7,8,9-tetrahydronaphth[2,3-b]-1,4-oxazin-3 (4H)-one In a mixture of 10 ml of glacial acetic acid with 1.25 ml of water, 2-(5,6,7,8-tetrahydro-3-nitro-2-naphthoxy)-propionic acid ethyl ester is dissolved and mixed in portions with 960 mg of iron powder. It is heated, cooled and poured onto water. The crystals are suctioned off and washed with water, dissolved again with ethyl acetate and washed with soda solution, the organic phase is washed with brine, dried with magnesium sulfate and concentrated by evaporation. 740 mg, yield 81%, results.

[1H]-NMR (CDCl$_3$): 9.61 br 1H, 6.69 s 1H, 6.51 s 1H, 4.61 q 1H, 2.68 m 4H and 1.75 m 4H, 1.56 d 3H.

The following are produced in the same way:
2-Ethyl-6,7,8,9-tetrahydro-naphth[2,3-b]-1,4-oxazin-3 (4H)-one
3-methyl-6,7,8,9-tetrahydro-naphth[2,1-b]-1,4-oxazin-2 (1H)-one
3-ethyl-6,7,8,9-tetrahydro-naphth[2,1-b]-1,4-oxazin-2 (1H)-one
6,7-cyclopenteno-2-methyl-1,4-benzoxazin-3-one
6,7-cyclopenteno-2-ethyl-1,4-benzoxazin-3-one
5,6-cyclopenteno-2-methyl-1,4-benzoxazin-3-one
5,6-cyclopenteno-2-ethyl-1,4-benzoxazin-3-one
6,7-(methylenedioxy)-2-methyl-1,4-benzoxazin-3-one
6,7-(methylenedioxy)-2-ethyl-1,4-benzoxazin-3-one
6-cyclohexyl-2-methyl-1,4-benzoxazin-3-one
7-(1-morpholinyl)-2-methyl-1,4-benzoxazin-3-one
6-keto-2-methyl-6,7,8,9-tetrahydro-naphth-[2,3-b]-1,4-oxazin-3-(4H)-one
7-keto-2-methyl-6,7,8,9-tetrahydro-naphth-[2,3-b]-1,4-oxazin-3-(4H)-one
8-keto-2-methyl-6,7,8,9-tetrahydro-naphth-[2,3-b]-1,4-oxazin-3-(4H)-one
2-methyl-6,7,8,9-tetrahydro-6,9-methano-naphth-[2,3-b]-1,4-oxazin-3-(4H)-one
6-keto-6,7-cyclopenteno-2-methyl-1,4-benzoxazin-3-one
6,6,9,9-tetramethyl-6,7,8,9-tetrahydro-naphth-[2,3-b]-1,4-oxazin-3-(4H)-one H) 5,6,7,8-Tetrahydro-3-amino-naphthalene-2-thiol 5,6,7,8-Tetrahydro-[2-(N,N-dimethylaminothiocarbamoyl)oxy]-3-nitronaphthalene is synthesized according to the instructions of Chem. Pharm. Bull. 1991, 39, 2888 and the literature that is mentioned there from 5,6,7,8-tetrahydro-3-nitronaphth-2-ol and N,N-dimethylaminothiocarbamoyl chloride. [1H]-NMR (CDCl$_3$): 7.87 s 1H, 6.92 s 1H, 3.48 s 3H and 3.39 s 3H, 2.85 m 4H and 1.85 m 4H.

The subsequent rearrangement at 180° C. yields 5,6,7,8-tetrahydro-[2-(N,N-dimethylaminocarbamoyl)thio]-3-nitronaphthalene. The yield is 80%. After reduction with lithium aluminum hydride, 5,6,7,8-tetrahydro-3-amino-naphthalene-2-thiol, which is used as crude product, is obtained from the above.

The following is produced in the same way:
6-Aminoindan-5-thiol.

According to instructions B), synthesis from the latter is done in an analogous manner:
2-Methyl-6,7,8,9-tetrahydro-naphtho[2,3-b]-1,4-thiazin-3(4H)-one
2-ethyl-6,7,8,9-tetrahydro-naphthor[2,3-b]-1,4-thiazin-3 (4H)-one
6,7-cyclopenteno-2-methyl-1,4-benzothiazin-3-one
6,7-cyclopenteno-2-ethyl-1,4-benzothiazin-3-one.

From the corresponding commercially available aminothiophenols, there are also obtained with this method:
6-Trifluoromethyl-2-methyl1,4-benzothiazin-3-one
6-trifluoromethyl-2-ethyl-1,4-benzothiazin-3-one
6-trifluoromethyl-2-propyl-1,4-benzothiazin-3-one I) 2-Nitro-4,5-(pentamethylene)phenol A solution of 3.2 g (20 mmol) of 4,5-(pentamethylene) phenol (V. Prelog, L. Ruzicka, O. Metzler, Helv. Chim. Acta 1947, 30, 1883) in 40 ml of glacial acetic acid is mixed with 1.3 g (20 mmol) of 100% nitric acid, and it is stirred for 1.5 hours at room temperature. The reaction mixture is diluted with water and extracted with ether. The combined ether extracts are washed with water, dried ($Na_2SO_4$) and concentrated by evaporation in a vacuum. Column chromatography on silica gel with hexane-ether yields 1.83 g of product (48% of theory).

Melting point 88° C.

Analogously produced is:

4,5-(Hexamethylene)-2-nitrophenol (41% of theory). $^1$H-NMR (CDCl$_3$): 1.37 (m, 4H), 1.60–1.78 (m, 4H), 2.75 (m, 4H), 6.90 (s, 1H), 7.84 (s, 1H), 10.47 (s, 1H).

J1) 2-[2-Nitro-4,5-(pentamethylene)phenoxy]-propionic acid-ethyl ester

A solution of 1.3 ml (8.25 mmol) of azodicarboxylic acid-diethyl ester and 1.46 ml (12.4 mmol) of lactic acid-ethyl ester in 15 ml of THF is added to a solution of 1.71 g (8.25 mmol) of 2-nitro-4,5-(pentamethylene)phenol and 2.16 g (8.25 mmol) of triphenylphosphine in 55 ml of THF. After three hours of stirring at room temperature, another 1.08 g (4.13 mmol) of triphenylphosphine, 0.65 ml (4.13 mmol) of azodicarboxylic acid-diethyl ester and 0.73 ml (6.19 mmol) of lactic acid ethyl ester are added to the above. After 2 hours, the reaction mixture is diluted with ethyl acetate (200 ml), washed with water (2×40 ml), dried ($Na_2SO_4$) and concentrated by evaporation in a vacuum. Column chromatography on silica gel with hexane-ether yields 2.27 g of product (90% of theory).

$^1$H-NMR (CDCl$_3$): 1.25 (t, 3H), 1.63 (m, 4H), 1.67 (d, 3H), 1.83 (m, 2H), 2.77 (m, 4H), 4.22 (q, 2H), 4.80 (q, 1H), 6.72 (s, 1H), 7.63 (s, 1H).

The following is obtained analogously:

2-[4,5-(Hexamethylene)-2-nitrophenoxy]propionic acid-ethyl ester (86% of theory), 1H-NMR (CDCl$_3$): 1.23 (t, 3H), 1.35 (m, 4H), 1.60–1.72 (m, 4H), 1.68 (d, 3H), 2.73 (m, 4H), 4.21 (qd, 2H), 4.82 (q, 1H), 6.71 (s, 1H), 7.64 (s, 1H).

According to the process that is mentioned here, enantiomer-pure compounds, such as (2S)-2-[2-nitro-4,5-(pentamethylene)phenoxy]propionic acid-ethyl ester or (2R)-2-[2-nitro-4,5-(pentamethylene)phenoxy]propionic acid-ethyl ester can be produced with ee of up to 98%, which can be used in further reactions.

J2) 2-Methyl-6,7-pentamethylene-1,4-dihydrobenzoxazin-3-one

A suspension of 2.20 g (7.2 mmol) of 2-[2-nitro-4,5-(pentamethylene)phenoxy]propionic acid-ethyl ester, 5.94 g (90.9 mmol) of zinc and 1.8 g of ammonium chloride in 400 ml of THF-ethanol-water (1:3:2) is stirred for 18 hours at room temperature. The batch is filtered, and the filtrate is concentrated by evaporation in a vacuum. Column chromatography. on silica gel with hexane-ether yields 1.53 g of product (93% of theory).

Melting point 215° C. Analogously:

6,7-Hexamethylene-2-methyl-1,4-dihydrobenzoxazin-3-one (73% of theory). Melting point 194–195° C.

J3) 6-(Propionyl)-2-methyl-1,4-benzoxazin-3-(4H)-one 13.3 g of aluminum(III) chloride is mixed drop by drop with 2.2 ml of-DMF. 1.63 g of 2-methyl-1,4-benzoxazin-3-(4H)-one is added in portions to it and then 1 equivalent of propionyl chloride is carefully added. Stirring of the mixture is continued at 70° C. After 3 hours, it is poured onto a lot of ice water, acidified, the crystals are washed with water, taken up in ethyl acetate, and this phase is washed again with water. After drying and concentration by evaporation, a yield of 89% is obtained.

[1H]-NMR (DMSO): 10.8 br 1H, 7.65 dd, 7.54 d, 7.10 d 1H each, 4.82 q 1H, 3.0 q 2H, 1.51 d 3H, 1.12 tr 3H.

The following are produced in the same way:

6-(Styrylcarboxy)-2-methyl-1,4-benzoxazin-3-(4H)-one 6-(3-carboxy-propionyl)-2-methyl-1,4-benzoxazin-3-(4H)-one 6-(4-ethoxycarbonyl-butyryl)-2-methyl-1,4-benzoxazin-3-(4H)-one 6-(2-chloroacetyl)-2-methyl-1,4-benzoxazin-3-(4H)-one K) 6-(1-Hydroxyprop-1-yl)-2-methyl-1,4-benzoxazin-3-(4H)-one 6-(Propionyl)-2-methyl-1,4-benzoxazin-3-(4H)-one (1.1 g) is stirred with a half equivalent of sodium borohydride in 30 ml of ethanol/THF 1:1 for three hours at room temperature. The mixture is poured onto water, extracted with ethyl acetate, the organic phase is dried with magnesium sulfate and concentrated by evaporation. A yield of 95% results.

For reaction to thione and amidine, carbinol is protected in the usual way as silyl ether, which is cleaved on the end product.

L) 6-Bromo-2-methyl-1,4-benzoxazin-3-(4H)-one

In 56 ml of glacial acetic acid, 6 g of 2-methyl-1,4-benzoxazin-3-(4H)-one is precooled at 0° C. and mixed drop by drop with 1.9 ml of bromine in 19 ml of glacial acetic acid. It is allowed to reach room temperature and stirred for another 8 hours. The mixture is poured onto ice water, the crystals are suctioned off and washed with water. 9.3 g of crude product results, which is recrystallized from ethanol/water. 7-Bromo-2-methyl-1,4-benzoxazin-3-(4H)-one is obtained as a by-product. As an alternative, 4-bromo-2-aminophenol can also be reacted according to the described processes.

M) 6-(2-Thienyl)-2-methyl-1,4-benzoxazin-3-(4H)-one 315 mg of 6-bromo-2-methyl-1,4-benzoxazin-3-(4H)-one is mixed in 4 ml of DME with 0.2 g of 2-thiopheneboronic acid and 150 mg of tetrakis-triphenylphosphine-palladium (O) and 340 mg of sodium bicarbonate (dissolved in 4 ml of water). It is stirred for some time at 100° C. The product is diluted with ethyl acetate, extracted 3 times with water, and dried with magnesium sulfate. It is concentrated by evaporation. The crude product is purified by column chromatography with a hexane/ethyl acetate mixture and yields pure 33% product.

The following are produced in the same way:

6-(3-Thienyl)-2-methyl-1,4-benzoxazin-3-(4H)-one 6-(3-pyridyl)-2-methyl-1,4-benzoxazin-3-(4H)-one from 3-pyridyldiethylborane 6-(styryl)-2-methyl-1,4-benzoxazin-3-(4H)-one from trans-styreneboronic acid.

N) 3-[2-Methyl-3-keto-1,4-benzoxazin-6-yl]-acrylamide 726 mg of 6-bromo-2-methyl-1,4-benzoxazin-3-(4H)-one is stirred in 1.5 ml of triethylamine with 0.267 g of acrylamide as well as 8 mg of palladium(II) acetate and 46 mg of tri-ortho-toluyl-phosphine for several hours at 100° C. The product is taken up in methanol and purified by column chromatography with an ethanol/ethyl acetate mixture. Yield 36%.

[1H]-NMR (DMSO): 10.7 br 1H, 7.4 to 7 br NH, 7.32 d 1H, 7.15 m 2H, 7.1 d 1H, 6.95 d 1H, 6.5 d J=16Hz 1H, 4.7 q 1H, 1.47 d7.

The following are produced in the same way:

3-[2-Methyl-3-keto-1,4-benzoxazin-7-yl]-acrylamide

3-[2-methyl-3-keto-1,4-benzoxazin-6-yl]-acrylonitrile

P) 2-Methyl-6-([1-methoxyimino]-prop-1-yl)-1,4-benzoxazin-3-one is obtained from 6-(propionyl)-2-methyl-1,4-benzoxazin-3-(4H)-one with O-methylhydroxylamine-hydrochloride.

Q)
The tosylate of carbinol is synthesized from 6-(propionyl)-2-methyl-1,4-benzoxazin-3-(4H)-one with toluenesulfonyl chloride in pyridine, reacted with sodium azide in DMSO to azide and reduced with tin(II) chloride to 2-methyl-6-(1-aminoprop-1-yl)-1,4-benzoxazin-3-one.

R)
2-Methyl-6-(1-methyl-1-hydroxy-prop-1-yl)-1,4-benzoxazin-3-one, which is etherified with tert-butyl-dimethylsilyl chloride, can be produced from 6-(propionyl)-2-methyl-1,4-benzoxazin-3-(4H)-one with methylmagnesium bromide in good yields.

S) 6-Phenyl-2-methyl-1,4-benzoxazine-3-thione 1.62 g of 6-phenyl-2-methyl-1,4-benzoxazin-3-one is heated with 0.5 g of phosphorus pentasulfide in 6 ml of pyridine p.a. The product is diluted with water, extracted 3 times with ethyl acetate, the organic phase is washed with brine and dried with magnesium sulfate. It is concentrated by evaporation. The crude product corresponds to a yield of 100%. Column chromatography with a hexane/ethyl acetate mixture yields pure product.

The following are produced in the same way:
6-Chloro-7-nitro-2-methyl-1,4-benzoxazine-3-thione
8-chloro-6-nitro-2-methyl-1,4-benzoxazine-3-thione
6-benzyl-2-methyl-1,4-benzoxazine-3-thione
5-nitro-2-methyl-1,4-benzoxazine-3-thione
6-nitro-2-methyl-1,4-benzoxazine-3-thione
7-nitro-2-methyl-1,4-benzoxazine-3-thione
6-nitro-2-ethyl-1,4-benzoxazine-3-thione
6-bromo-2-methyl-1,4-benzoxazine-3-(4H)-thione
7-nitro-2-ethyl-1,4-benzoxazine-3-thione
6-cyano-2-methyl-1,4-benzoxazine-3-thione
6-trifluoromethyl-2-methyl-1,4-benzoxazine-3-thione
9-H-fluoreno-[2,3-b]-2-methyl-1,4-oxazine-3-thione
1H-naphtho[2,1-b]-3-methyl-1,4-benzoxazine-2-thione
1H-naphth[2,1-b]-3-ethyl-1,4-benzoxazine-2-thione
4H-naphth[2,3-b]-2-methyl-1,4-benzoxazine-3-thione
4H-naphth[2,3-b]-2-ethyl-1,4-benzoxazine-3-thione
4H-naphtho[2,3-b]-1,4-benzoxazine-3-thione
4H-naphtho[2,3-b]-2-propyl-1,4-oxazine-3-thione
4H-naphtho[1,2-b]-2-methyl-1,4-oxazine-3-thione
4H-naphth[1,2-b]-2-ethyl-1,4-oxazine-3-thione
6-(imidazol-1-yl)-7-nitro-2-methyl-1,4-benzoxazine-3-thione
6,7-cyclopenteno-2-methyl-1,4-benzoxazine-3-thione
6,7-cyclopenteno-2-ethyl-1,4-benzoxazine-3-thione
5,6-cyclopenteno-2-methyl-1,4-benzoxazine-3-thione
5,6-cyclopenteno-2-ethyl-1,4-benzoxazine-3-thione
6,7-(methylenedioxy)-2-methyl-,4-benzoxazine-3-thione
6,7-(methylenedioxy)-2-ethyl-1,4-benzoxazine-3-thione
6-cyclohexyl-2-methyl-1,4-benzoxazine-3-thione
7-(1-morpholinyl)-2-methyl-1,4-benzoxazine-3-thione
2-ethyl-6,7,8,9-tetrahydro-naphth[2,3-b]-1,4-oxazine-3 (4H)-thione
2-methyl-6,7,8,9-tetrahydro-naphth[2,3-b]-1,4-oxazine-3 (4H)-thione
3-methyl-6,7,8,9-tetrahydronaphth[2,1-b]-1,4-oxazine-2 (1H)-thione
3-ethyl-6,7,8,9-tetrahydronaphth[2,1-b]-1,4-oxazine-2 (1H)-thione
2-Methyl-6,7,8,9-tetrahydro-naphtho[2,3-b]-1,4-thiazine-3(4H)-thione
2-ethyl-6,7,8,9-tetrahydro-naphtho[2,3-b]-1,4-thiazine-3 (4H)-thione
6,7-cyclopenteno-2-methyl-1,4-benzothiazine-3-thione
6,7-cyclopenteno-2-ethyl-1,4-benzothiazine-3-thione
6-trifluoromethyl-2-methyl-1,4-benzothiazine-3-thione
6-trifluoromethyl-2-ethyl-1,4-benzothiazine-3-thione
6-trifluoromethyl-2-propyl-1,4-benzothiazine-3-thione
6-Keto-2-methyl-6,7,8,9-tetrahydro-naphth-1,4-oxazine-3-(4H)-thione
7-keto-2-methyl-6,7,8,9-tetrahydro-naphth-1,4-oxazine-3-(4H)-thione
8-keto-2-methyl-6,7,8,9-tetrahydro-naphth-1,4-oxazine-3-(4H)-thione
2-methyl-6,7,8, 9-tetrahydro-6,9-methano-naphth-1,4-oxazine-3-(4H)-thione
6-keto-6,7-cyclopenteno-2-methyl-1,4-benzoxazine-3-thione
6,6,9,9-tetramethyl-6,7,8,9-tetrahydro-naphth-[2,3-b]-1,4-oxazine-3-(4H)-thione
3-[2-Methyl-3-thio-1,4-benzoxazin-6-yl]-acrylamide
3-[2-methyl-3-thio-1,4-benzoxazin-6-yl]-acrylonitrile
6-(2-Thienyl)-2-methyl-1,4-benzoxazine-3-(4H)-thione
6-(3-thienyl)-2-methyl-1,4-benzoxazine-3-(4H)-thione
6-(3-pyridyl)-2-methyl-1,4-benzoxazine-3-(4H)-thione
6-(styryl)-2-methyl-1,4-benzoxazine-3-(4H)-thione
6-(propionyl)-2-methyl-1,4-benzoxazine-3-(4H)-thione
6-(styrylcarboxy)-2-methyl-1,4-benzoxazine-3-(4H)-thione
6-(3-carboxy-propionyl)-2-methyl-1,4-benzoxazine-3-(4H)-thione
6-(4-ethoxycarbonyl-butyryl)-2-methyl-1,4-benzoxazine-3-(4H)-thione
6-(2-chloroacetyl)-2-methyl-1,4-benzoxazine-3-(4H)-thione S1) 2-Methyl-6,7-pentamethylene-1,4-dihydrobenzoxazine-3-thione A solution of 0.41 g (1.8 mmol) of 2-methyl-6,7-pentamethylene-1,4-dihydrobenzoxazin-3-one in 40 ml of DME is mixed with 0.78 g (1.9 mmol) of Lawesson's reagent. After 5 hours of stirring at room temperature, the batch is concentrated by evaporation in a vacuum. Column chromatography on silica gel with hexane-ether yields 0.27 g of product (63% of theory). $^1$H-NMR (CDCl$_3$): 1.52–1.70 (m, 4H), 1.61 (d, 3H), 1.80 (m, 2H), 2.71 (m, 4H), 4.98 (q, 1H), 6.61 (s, 1H), 6,72 (s, 1H), 9.83 (br.s, 1H).

Analogously produced is:
6,7-Hexamethylene-2-methyl-1,4-dihydrobenzoxazine-3-thione
(83% of theory) $^1$H-NMR (CDCl$_3$): 1.37 (m, 4H), 1.55–1.73 (m, 4H), 1.63 (d, 3H), 2.69 (t, 4H), 4.98 (q, 1H), 6.60 (s, 1H), 6.75 (s, 1H), 9.64 (br.s, 1H).

T) 6-Amino-2-ethyl-1,4-benzoxazine-3-thione 1 g of 6-nitro-2-ethyl-1,4-benzoxazine-3-thione is dissolved with 7.6 ml of glacial acetic acid and 1 ml of water, and it is mixed with 950 mg of iron powder. After several hours at room temperature, it is poured onto water. The crystals are suctioned off and washed with water, dissolved again with ethyl acetate and washed neutral with brine, the organic phase is dried with magnesium sulfate and concentrated by evaporation. After column chromatography with hexane/ethyl acetate, a yield of 811 mg results.

The following are produced in the same way:
5-Amino-2-ethyl-1,4-benzoxazine-3-thione 5-amino-2-methyl-1,4-benzoxazine-3-thione
6-amino-2-methyl-1,4-benzoxazine-3-thione
7-amino-2-methyl-1,4-benzoxazine-3-thione U) N-[(2-Ethyl-1,4-benzoxazine-3-thion-6-yl]-phenylcarboximidamide hydroiodide 201 mg of S-methylthio-benzamide hydroiodide is added to 150 mg of 6-amino-2-ethyl-1,4-benzoxazine-3-thione in 3 ml of isopropanol, and it is refluxed for 4 hours. The crude product can be concentrated by evaporation and used for subsequent reactions.

The following are produced in the same way (partially as hydroiodides):

N-[(2-Methyl-1,4-benzoxazine-3-thion-7-yl]-4-methylphenylcarboximidamide
N-[(2-ethyl-1,4-benzoxazine-3-thion-7-yl]-4-methylphenylcarboximidamide
N-[(2-methyl-1,4-benzoxazine-3-thion-6-yl]-4-methylphenylcarboximidamide
N-[(2-ethyl-1,4-benzoxazine-3-thion-6-yl]-4-methylphenylcarboximidamide
N-[(2-methyl-1,4-benzoxazine-3-thion-7-yl]-phenylcarboximidamide
N-[(2-ethyl-1,4-benzoxazine-3-thion-7-yl]-phenylcarboximidamide
N-[(2-methyl-1,4-benzoxazine-3-thion-6-yl]-phenylcarboximidamide
N-[(2-methyl-1,4-benzoxazine-3-thion-7-yl]-2,4-dichlorophenylcarboximidamide
N-[(2-ethyl-1,4-benzoxazine-3-thion-7-yl]-2,4-dichlorophenylcarboximidamide
N-[(2-methyl-1,4-benzoxazine-3-thion-6-yl]-2,4-dichlorophenylcarboximidamide
N-[(2-ethyl-1,4-benzoxazine-3-thion-6-yl]-2,4-dichlorophenylcarboximidamide
N-[(2-methyl-1,4-benzoxazine-3-thion-7-yl]-(2-thienyl)-carboximidamide
N-[(2-ethyl-1,4-benzoxazine-3-thion-7-yl]-(2-thienyl)carboximidamide
N-[(2-methyl-1,4-benzoxazine-3-thion-6-yl]-(2-thienyl)-carboximidamide
N-[(2-ethyl-1,4-benzoxazine-3-thion-6-yl]-(2-thienyl)carboximidamide V) 2-Ethyl-6-(1-pyrrolo)-1,4-benzoxazine3-thione 1 equivalent of 2,5-dimethoxytetrahydrofuran is added to 100 mg of 6-amino-2-ethyl-1,4-benzoxazine-3-thione in 1 ml of acetic acid, and it is refluxed. The mixture is poured onto soda solution, extracted with ethyl acetate, the organic phase is washed neutral, dried with magnesium sulfate and concentrated by evaporation. 77 mg of product, which is further used, results.

W) N-[(2-Ethyl-1,4-benzoxazine-3-thio-6-yl]-phenylurea

A small excess of phenylisocyanate is added to 150 mg of 6-amino-2-ethyl-1,4-benzoxazine-3-thione in 2 ml of THF, and it is stirred at ice bath temperature for 4 hours. The crude product can be concentrated by evaporation and used for subsequent reactions.

Using the isocyanates or isothiocyanates, the following are produced in the same way:

N-[6-(2-Ethyl-3-thio-1,4-benzoxazinyl)-N-phenylthiourea
N-[6-(2-methyl-3-thio-1,4-benzoxazinyl)-N-phenylurea
N-[6-(2-methyl-3-thio-1,4-benzoxazinyl)-N-phenylthiourea
N-[6-(2-ethyl)-3-thio-1,4-benzoxazinyl)-N-cyclohexylurea
N-[6-(2-ethyl-3-thio-1,4-benzoxazinyl)-N-2-methyl-4-chlorophenylurea
N-[6-(2-ethyl-3-thio-1,4-benzoxazinyl)-N-2-chlorophenylurea
N-[7-(2-ethyl-3-thio-1,4-benzoxazinyl)-N-phenylthiourea
N-[7-(2-methyl-3-thio-1,4-benzoxazinyl)-N-phenylurea
N-[7-(2-ethyl-3-thio-1,4-benzoxazinyl)-N-phenylurea
N-[7-(2-methyl-3-thio-1,4-benzoxazinyl)-N-phenylthiourea
N-[7-(2-ethyl-3-thio-1,4-benzoxazinyl)-N-cyclohexylurea
N-[7-(2-ethyl-3-thio-1,4-benzoxazinyl)-N-2-methyl-4-chlorophenylurea
N-[7-(2-ethyl-3-thio-1,4-benzoxazinyl)-N-2-chlorophenylurea

EXAMPLE 1

6-Phenyl-2-methyl-3-amino-1,4-benzoxazine 1.7 g of 6-phenyl-2-methyl-1,4-benzoxazine-3-thione is stirred into 10 ml of saturated ammonia solution in methanol (commercially available). After 2 days at room temperature, 100% crude product is obtained after concentration by evaporation. Using column chromatography with hexane/ethyl acetate, the product is purified. A yield of 59% results.

[1H]-NMR (DMSO): 7.58 m 2H, 7.42 dd 2H, 7.3 m 1H, 7.10 m 2H, 6.85 d 1H, 6.7 br NH, 4.71 q 1H, 1.32 d 3H.

The following are produced in the same way:

6-Chloro-7-nitro-2-methyl-3-amino-1,4-benzoxazine
[1H]-NMR (DMSO): 7.53 s 1H, 7.01 s 1H, 4.82 q 1H, 1.33 d 3H.

6-Methylthio-7-nitro-2-methyl-3-amino-1,4-benzoxazine
6-methoxy-7-nitro-2-methyl-3-amino-1,4-benzoxazine
6-(imidazol-1-yl)-7-nitro-2-methyl-3-amino-1,4-benzoxazine
8-chloro-6-nitro-2-methyl-3-amino-1,4-benzoxazine
[1H]-NMR (DMSO): 7.4 br 2H, 7.55 d 1H, 7,81 d 1H, 5.02 q 1H, 1.38 d 3H.

6-Benzyl-2-methyl-3-amino-1,4-benzoxazine
5-nitro-2-methyl-3-amino-1,4-benzoxazine
6-nitro-2-methyl-3-amino-1,4-benzoxazine
7-nitro-2-methyl-3-amino-1,4-benzoxazine
6-nitro-2-ethyl-3-amino-1,4-benzoxazine
7-nitro-2-ethyl-3-amino-1,4-benzoxazine
6-cyano-2-methyl-3-amino-1,4-benzoxazine
6-trifluoromethyl-2-methyl-3-amino-1,4-benzoxazine
9-H-fluoreno-[2,3-b]-3-amino-2-methyl-1,4-oxazine
1H-naphtho[2,1-b]methyl-3-amino-1,4-oxazine
1H-naphth[2,1-b]ethyl-3-amino-1,4-oxazine
4H-naphtho[2,3-b]-2-methyl-3-amino-1,4-oxazine
4H-naphth[2,3-b]-2-ethyl-3-amino-1,4-oxazine
4H-naphth[2,3-b]-3-amino-1,4-oxazine
4H-naphtho[2,3-b]-2-n-propyl-3-amino-1,4-oxazine
4H-naphtho[1,2-b]-2-methyl-3-amino-1,4-oxazine
4H-naphth[1,2-b]-2-ethyl-3-amino-1,4-oxazine
6,7-cyclopenteno-2-methyl-3-amino-1,4-benzoxazine
[1H]-NMR (DMSO): 6.71 s 1H, 6.63 s 1H, 6.5 br NH, 4.59 q 1H, 2.75 m 4H, 1.95 pentet 2H, 1.7 m 2H, 1.25 d 3H.
6,7-Cyclopenteno-2-ethyl-3-amino-1,4-benzoxazine

[1H]-NMR (DMSO): 6.85 s 1H, 6.72 s 1H, 4.34 dd 1H, 2.8 m 4H, 2.05 pentet 2H, 1.7 m 2H, 1.05 tr 3H.

5,6-Cyclopenteno-2-methyl-3-amino-1,4-benzoxazine
5,6-cyclopenteno-2-ethyl-3-amino-1,4-benzoxazine
6,7-(methylenedioxy)-2-methyl-3-amino-1,4-benzoxazine

[1H]-NMR (DMSO): 6.5 br NH, 6.5 2×s 2H, 5.87 s 2H, 4.55 q 1H, 1.25 d 3H.

6,7-(Methylenedioxy)-2-ethyl-3-amino-1,4-benzoxazine
6-cyclohexyl-2-methyl-3-amino-1,4-benzoxazine

[1H]-NMR (DMSO): 6.6 br NH, 6.7 m 3H, 4.41 q 1H, 2.85 m 1H, 1.8 to 1.1 m 12H, 0.92 tr 3H.

7-(1-Morpholinyl)-2-methyl-3-amino-1,4-benzoxazine
2-ethyl-3-amino-6,7,8,9-tetrahydro-naphth[2,3-b]-1,4-oxazine
2-methyl-3-amino-6,7,8,9-tetrahydro-naphth[2,3-b]-1,4-oxazine (1H]-NMR (CDCl$_3$): 6.75 s 1H, 6.56 s 1H, 4.59 q 1H, 2.7 m 4H and 1.8 m 4H, 1.50 d 3H.

3-Methyl-2-amino-6,7,8,9-tetrahydronaphth[2,1-b]-1,4-oxazine
3-ethyl-2-amino-6,7,8,9-tetrahydronaphth[2,1-b]-1,4-oxazine
6-keto-3-amino-2-methyl-6,7,8,9-tetrahydronaphth-1,4-oxazine
7-keto-3-amino-2-methyl-6,7,8,9-tetrahydro-naphth-1,4-oxazine
8-keto-3-amino-2-methyl-6,7,8,9-tetrahydro-naphth-1,4-oxazine
2-methyl-3-amino-6,7,8,9-tetrahydro-6,9-methano-naphth-1,4-oxazine
3-amino-6-keto-6,7-cyclopenteno-2-methyl-1,4-benzoxazine
6,6,9,9-tetramethyl-6,7,8,9-tetrahydro-3-amino-2-methyl-[2,3-b]-naphth-1,4-oxazine
2-methyl-3-amino-6,7,8,9-tetrahydro-naphtho2,3-b]-1,4-thiazine
2-ethyl-3-amino-6,7,8,9-tetrahydro-naphtho[2,3-b]-1,4-thiazine
3-Amino-2-methyl-6,7-(pentamethylene-1,4-(2H)benzoxazine 0.23 g (0.93 mmol) of (2R)-2-methyl-6,7-pentamethylene-1,4-dihydrobenzoxazine-3-thione is dissolved in 20 ml of 7N methanolic ammonia solution. After 5 hours, the batch is concentrated by evaporation, and the residue is purified by column chromatography on silica gel with ethyl acetate as an eluant: 0.20 g of product (95% of theory).

$^1$H-NMR (CDCl$_3$): 1.48 (d, 3H), 1.53–1.71 (m, 4H), 1.81 (m, 2H), 2.71 (m, 4H), 4.57 (q, 1H), 6.62 (s, 1H), 6.78 (s, 1H).

Analogously:

3-Amino-6,7-hexamethylene-2-methyl-1,4-(2H)benzoxazine (57% of theory) of $^1$H-NMR (CDCl$_3$): 1.35 (m, 4H), 1.47 (d, 3H), 1.63 (m, 4H), 2.66 (t, 4H), 4.58 (q, 1H), 6.60 (s, 1H), 6,77 (s, 1H).

6,7-Cyclopenteno-2-methyl-3-amino-1,4-benzothiazine

[1H]-NMR (DMSO): 6.6 br NH, 7.01 s 1H, 6,79 s 1H, 3.45 q 1H, 2.8 m 4H, 2.0 m 2H, 1.13 d 3H.

6,7-Cyclopenteno-2-ethyl-3-amino-1,4-benzothiazine
6-trifluoromethyl-2-methyl-3-amino-1,4-benzothiazine
6-trifluoromethyl-2-ethyl-3-amino-1,4-benzothiazine
6-trifluoromethyl-2-propyl-3-amino-1,4-benzothiazine
N-[(2-methyl-1,4-benzoxazin-3-amino-7-yl]-(2-thienyl)carboximidamide

[1H]-NMR (DMSO): 6.6 br NH, 7.72 m, 7.61 d, 7.10 dd, 6.8 d, 6.42 d, 6.32 m at 1H each, 4.63 q 1H, 1.31 d 3H.

N-[(2-Ethyl-1,4-benzoxazin-3-amino-7-yl]-(2-thienyl)carboximidamide
N-[(2-methyl-1,4-benzoxazin-3-amino-6-yl]-(2-thienyl)carboximidamide
N-[(2-ethyl-1,4-benzoxazin-3-amino-6-yl]-(2-thienyl)carboximidamide
N-[(2-methyl-1,4-benzoxazin-3-amino-7-yl]-4-methylphenylcarboximidamide
N-[(2-ethyl-1,4-benzoxazin-3-amino-7-yl]-4-methylphenylcarboximidamide
N-[(2-methyl-1,4-benzoxazin-3-amino-6-yl]-4-methylphenylcarboximidamide
N-[(2-ethyl-1,4-benzoxazin-3-amino-6-yl]-4-methylphenylcarboximidamide
N-[(2-methyl-1,4-benzoxazin-3-amino-7-yl]-phenylcarboximidamide
N-[(2-ethyl-1,4-benzoxazin-3-amino-7-yl]-phenylcarboximidamide
N-[(2-methyl-1,4-benzoxazin-3-amino-6-yl]-phenylcarboximidamide
N-[(2-ethyl-1,4-benzoxazin-3-amino-6-yl]-phenylcarboximidamide
N-[(2-methyl-1,4-benzoxazin-3-amino-7-yl]-2,4-dichlorophenylcarboximidamide
N-[(2-ethyl-1,4-benzoxazin-3-amino-7-yl]-2,4-dichlorophenylcarboximidamide
N-[(2-methyl-1,4-benzoxazin-3-amino-6-yl]-2,4-dichlorophenylcarboximidamide
N-[(2-ethyl-1,4-benzoxazin-3-amino-6-yl]-2,4-dichlorophenylcarboximidamide hydrochloride

[1H]-NMR (DMSO): 9.5 broad, 7.97 m 2H, 7.74 dd 1H, 7.40 d 1H, 7.27 d 1H, 7.20 dd 1H, 5.23 q 1H, 1.8 m 2H, 1.05 tr 3H.

N-[6-(2-Ethyl-3-amino-1,4-benzoxazinyl)-N-phenylurea
N-[6-(2-ethyl-3-amino-1,4-benzoxazinyl)-N-phenylthiourea

[1H]-NMR (DMSO): 9.6 br NH, 7.5 m 2H, 7.3 m 2H, 7.1 dd 1H, 6.7 to 6.9 m about 5H, 4.45 dd 1H, 1.6 m 2H, 0.93 tr 3H.

N-[6-(2-Methyl-3-amino-1,4-benzoxazinyl)-N-phenylurea
N-[6-(2-methyl-3-amino-1,4-benzoxazinyl)-N-phenylthiourea
N-[6-(2-ethyl-3-amino-1,4-benzoxazinyl)-N-cyclohexylurea
N-[6-(2-ethyl-3-amino-1,4-benzoxazinyl)-N-2-methyl-4-chlorophenylurea
N-[6-(2-ethyl-3-amino-1,4-benzoxazinyl)-N-2-chlorophenylurea
N-[7-(2-ethyl-3-amino-1,4-benzoxazinyl)-N-phenylurea
N-[7-(2-ethyl-3-amino-1,4-benzoxazinyl)-N-phenylthiourea
N-[7-(2-methyl-3-amino-1,4-benzoxazinyl)-N-phenylurea
N-[7-(2-methyl-3-amino-1,4-benzoxazinyl)-N-phenylthiourea
N-[7-(2-ethyl-3-amino-1,4-benzoxazinyl)-N-cyclohexylurea N-[7-(2-ethyl-3-amino-1,4-benzoxazinyl)-N-2-methyl-4-chlorophenylurea N-[7-(2-ethyl-3-amino-1,4-benzoxazinyl)-N-2-chlorophenylurea 2-Methyl-3-amino-6-(2-thienyl)-1,4-benzoxazine
[1H]-NMR (CDCl$_3$): 7.3 to 7.0 m 6H, 4.55 q 1H, 1.52 d 3H.

2-Methyl-3-amino-6-(3-thienyl)-1,4-benzoxazine

3-[2-methyl-3-amino-1,4-benzoxazin-6-yl]-acrylamide

3-[2-methyl-3-amino-1,4-benzoxazin-6-yl]-acrylonitrile 2-methyl-3-amino-6-(3-pyrido)-1,4-benzoxazine 2-methyl-3-amino-6-(1-pyrrolo)-1,4-benzoxazine 6-(Propionyl)-3-amino-2-methyl-1,4-benzoxazine
[1H]-NMR (DMSO): 6.8 br NH, 7.5 d 1H, 7.46 d 1H, 6.88 d 1H, 4.77 q 1H, 2.95 tr 2H, 1.33 d 3H, 1.11 tr 3H.

6-(Styrylcarboxy)-3-amino-2-methyl-1,4-benzoxazine 6-(3-carboxy-propionyl)-3-amino-2-methyl-1,4-benzoxazine 6-(4-ethoxycarbonyl-butyryl)-3-amino-2-methyl-1,4-benzoxazine 6-(2-chloroacetyl)-3-amino-2-methyl-1,4-benzoxazine 2-methyl-3-amino-6-(1-hydroxyprop-1-yl)-1,4-benzoxazine
[1H]-NMR (CDCl$_3$): 7.0 d, 6.91 dd, 6.82 d at 1H each, 4.60 q 1H, 4.52 tr 1H, 1.8 m 2H, 1.49 d 3H, 0.9 tr 3H.

2-Methyl-3-amino-6-([1-methoxyimino]-prop-1-yl)-1,4-benzoxazine 2-methyl-3-amino-6-(1-aminoprop-1-yl)-1,4-benzoxazine 2-methyl-3-amino-6-(1-methyl-1-hydroxy-prop-1-yl)-1,4-benzoxazine Starting Compounds (2)

4-Hydroxy-3-nitrobenzaldehyde-ethylenacetal 25 g of 4-hydroxy-3-nitrobenzaldehyde is mixed in toluene with 1.1 equivalents of ethylene glycol and 370 mg of paratoluenesulfonic acid. It is boiled for 4 hours in a water separator. The mixture is poured onto sodium bicarbonate solution, extracted with ethyl acetate, the organic phase is washed with brine, dried with magnesium sulfate and concentrated by evaporation. 23.6 g of crude product, which is suitable for further reactions, results.

2-(4-(1,3-Dioxolan-2-yl)-2-nitrophenoxy)propionic acid ethyl ester 23 g of 4-hydroxy-3-nitrobenzaldehyde-ethylenacetal is dissolved in 150 ml of DMF, and 20.6 g of potassium carbonate as well as 1.1 equivalents of D,L-2-bromopropionic acid ethyl ester in 20 ml of THF are added to it at 5° C. It is stirred for 14 hours. The mixture is poured onto water, extracted with ethyl acetate, the organic phase is dried with magnesium sulfate and concentrated by evaporation. 42 g of crude product, which is recrystallized, results. The yield is quantitative.

The following are produced analogously:

2-(4-(1,3-Dioxolan-2-yl)-2-nitrophenoxy)butyric acid ethyl ester 2-(4-(1,3-dioxolan-2-yl)-2-nitrophenoxy)pentanoic acid ethyl ester 6-Formyl-2-methyl-2H-1,4-benzoxazin-3-one 28.8 g of pulverized iron is added in portions to 34 g of 2-(4-(1,3-dioxolan-2-yl)-2-nitrophenoxy)propionic acid ethyl ester in 360 ml of glacial acetic acid with 80 ml of water while being cooled in an ice bath. The mixture is hot. After 2 hours, it is poured onto 1 l of water, extracted with ethyl acetate, and the organic phase is washed with brine. It is dried with magnesium sulfate and concentrated by evaporation. 20.3 g of brownish solid results.

[1H]-NMR (CDCl$_3$): 9.9 1H aldehyde, 9.36 br 1H, 7.75 dd 1H, 7.42 d 1H, 7.11 d 1H, 4.80 q 1H, 1.64 d 3H.

The following are produced according to the same process:

6-Formyl-2-ethyl-1,4-benzoxazin-3-one 6-formyl-2-propyl-1,4-benzoxazin-3-one

2-Methyl-3-oxo-6-(2-nitro-ethenyl)-3,4-dihydro-2H-1,4-benzoxazine 10 g (52.31 mmol) of [2-methyl-3-oxo-3,4-dihydro-2H-1,4-benzoxazin-6-yl]-carbaldehyde is refluxed in 37 ml of glacial acetic acid with 10 ml of nitromethane and 3.71 g of ammonium acetate for two hours. The reaction mixture is added to ice water, and the precipitated product is suctioned off, washed neutral with water and used in the next stage after drying without further purification (yield 93%).

2-Methyl-3-oxo-6-(2-amino-ethyl)-3,4-dihydro-2H-1,4-benzoxazine 2 g (8.5 mmol) of 2-methyl-3-oxo-6-(2-nitro-ethenyl)-3,4-dihydro-2H-1,4-benzoxazine is mixed with 80 ml of acetic acid and 1.6 ml of concentrated sulfuric acid and, after 200 mg of platinum dioxide is added, it is reduced in an autoclave. The catalyst is then suctioned off, and the batch is spun in until a dry state is reached. The remaining residue is chromatographed on silica gel (mobile solvent: isopropanol/ammonia). 923.5 mg (52.4%) of the described compound is obtained.

6-((Thien-2-yl)-methylaminomethyl)-2-methyl-1,4-benzoxazin-3-one

In 4 ml of a mixture of methanol and THF, 193 mg of 6-formyl-2-methyl-1,4-benzoxazin-3-one is dissolved and mixed with 113 mg of 2-(aminomethyl)-thiophene. It is stirred for 30 minutes at room temperature and then 0.6 equivalent of potassium borohydride is added. After three hours at room temperature, it is poured onto water, extracted with ethyl acetate, and the organic phase is washed with brine. It is dried with magnesium sulfate and concentrated by evaporation. 248 mg (86%) of crude product, which is provided with a protective group, is obtained.

[1H]-NMR (CDCl$_3$): 9.4 br 1H, 6.8 to 7.3 6H, 4.64 q 1H, 4.0 s 2H, 3.73 s 2H, 1.59 d 3H.

The following are produced in the same way:

6-((Thien-3-yl)-methylaminomethyl)-2-methyl-1,4-benzoxazin-3-one 6-(benzylaminomethyl)-2-methyl-1,4-benzoxazin-3-one 6-((4-methoxybenzyl)aminomethyl)-2-methyl-1,4-benzoxazin-3-one 6-((3-chlorobenzyl)aminomethyl)-2-methyl-1,4-benzoxazin-3-one 6-((2-chloro-6-fluorobenzyl)aminomethyl)-2-methyl-1,4-benzoxazin-3-one 6-((4-chlorobenzyl)aminomethyl)-2-methyl-1,4-benzoxazin-3-one 6-((3,4-dichlorobenzyl)aminomethyl)-2-methyl-1,4-benzoxazin-3-one 6-((2-chlorobenzyl)aminomethyl)-2-methyl-1,4-benzoxazin-3-one 6-((2,4-dichlorobenzyl)aminomethyl)-2-methyl-1,4-benzoxazin-3-one 6-((2,3-dimethylbenzyl)aminomethyl)-2-methyl-1,4-benzoxazin-3-one 6-((3-fluorobenzyl)aminomethyl)-2-methyl-1,4-benzoxazin-3-one 6-((indan-1-yl)aminomethyl)-2-methyl-1,4-benzoxazin-3-one 6-((indan-2-yl)aminomethyl)-2-methyl-1,4-benzoxazin-3-one 6-((cyclohexylmethyl)aminomethyl)-2-methyl-1,4-benzoxazin-3-one 6-((1,2,3,4-tetrahydronaphth-1-yl)aminomethyl)-2-methyl-1,4-benzoxazin-3-one 6-((diphenylmethyl)aminomethyl)-2-methyl-1,4-benzoxazin-3-one 6-((3-methoxybenzyl)aminomethyl)-2-methyl-1,4-benzoxazin-3-one 6-((3-nitrobenzyl)aminomethyl)-2-methyl-1,4-benzoxazin-3-one 6-((4-nitrobenzyl)aminomethyl)-2-methyl-1,4-benzoxazin-3-one 6-((4-sulfamoylbenzyl)aminomethyl)-2-methyl-1,4-benzoxazin-3-one 6-((4-methylsulfonylbenzyl)aminomethyl)-2-methyl-1,4-benzoxazin-3-one 6-((4-fluorobenzyl)aminomethyl)-2-methyl-1,4-benzoxazin-3-one 6-((4-dimethylaminobenzyl)aminomethyl)-2-methyl-1,4-benzoxazin-3-one 6-((3,4-methylenedioxybenzyl)aminomethyl)-2-methyl-1,4-benzoxazin-3-one 6-((2-fluorobenzyl)aminomethyl)-2-methyl-1,4-benzoxazin-3-one 6-((4-methylbenzyl)aminomethyl)-2-methyl-1,4-benzoxazin-3-one 6-((4-pyridyl)-methylaminomethyl)-2-methyl-1,4-benzoxazin-3-one 6-((3-pyridyl)-methylaminomethyl)-2-methyl-1,4-benzoxazin-3-one 6-((2-furyl)-methylaminomethyl)-2-methyl-1,4-benzoxazin-3-one 6-((naphth-1-yl)-methylaminomethyl)-2-methyl-1,4-benzoxazin-3-one 6-((3-trifluoromethylbenzyl)aminomethyl)-2-methyl-1,4-benzoxazin-3-one 6-((thien-2-yl)-methylaminomethyl)-2-ethyl-1,4-benzoxazin-3-one 6-(benzylaminomethyl)-2-ethyl-1,4-benzoxazin-3-one 6-((thien-2-yl)-methylaminomethyl)-2-propyl-1,4-benzoxazin-3-one 6-(benzylaminomethyl)-2-propyl-1,4-benzoxazin-3-one The following are obtained accordingly:
From 6-(propionyl)-2-methyl-1,4-benzoxazin-3-(4H)-one:

6-(1-(Benzylamino)-prop-1-yl)-2-methyl-1,4-benzoxazin-3-one 6-(1-((thien-2-yl)-methylamino)-prop-1-yl)-2-methyl-1,4-benzoxazin-3-one From 6-(2-ketoprop-1-yl)-2-methyl-1,4-benzoxazin-3-(4H)-one:

6-(2-(Benzylamino)-prop-1-yl)-2-methyl-1,4-benzoxazin-3-one

Obtained from 6-oxo-6,7-cyclopenteno-2-methyl-1,4-benzoxazin-3-one (German File Number 197 40 386.7) are 6-(benzylamino)-6,7-cyclopenteno-2-methyl-1,4-benzoxazin-3-one 6-(3-chlorobenzylamino)-6,7-cyclopenteno-2-methyl-1,4-benzoxazin-3-one and obtained analogously from the ketone 6-oxo-6,7-cyclohexeno-2-methyl-1,4-benzoxazin-3-one are:

6-(Benzylamino)-6,7-cyclohexeno-2-methyl-1,4-benzoxazin-3-one 6-(3-chlorobenzylamino)-6,7-cyclohexeno-2-methyl-1,4-benzoxazin-3-one and analogously produced from the ketone 7-oxo-6,7-cyclohexeno-2-methyl-1,4-benzoxazin-3-one, which was produced as 6-oxo-6,7-cyclohexeno-2-methyl-1,4-benzoxazin-3-one from 6-methoxy-2-tetralon, 7-(3-chlorobenzylamino)-6,7-cyclohexeno-2-methyl-1,4-benzoxazin-3-one.

2-Methyl-3-oxo-6-[2-(3-chlorobenzylamino)-ethyl]-3,4-dihydro-2H-1,4-benzoxazine 915 mg (4.437 mmol) of 2-methyl-3-oxo-6-(2-aminoethyl)-3,4-dihydro-2H-1,4-benzoxazine is dissolved in 16 ml of a methanol/tetrahydrofuran mixture (4:1). After adding 623.7 mg (4.437 mmol) of 3-chlorobenzaldehyde, the batch is stirred for two hours at room temperature. Then, 91.1 mg (2.408 mmol) of sodium borohydride is added in portions and stirred for another two hours at room temperature. The batch is added to 50 ml of water, and after three-fold extraction with ethyl acetate, the combined organic extracts are washed with brine, dried and the solvent is spun off. The remaining residue is chromatographed on silica gel (mobile solvent: ethyl acetate/methanol). Yield 584.6 mg (39.8%).

6-((Thien-2-yl)-methyl-(tert-butyloxycarbonyl)aminomethyl)-2-methyl-1,4-benzoxazin-3-one The product is obtained by reaction of 6-((thien-2-yl)-methylaminomethyl)-2-methyl-1,4-benzoxazin-3-one (245 mg) in 5 ml of dichloromethane with the addition of 0.177 ml of triethylamine and 223 mg of di-tert-butyldicarbonate. After 12 hours at room temperature, the reaction is completed. It is diluted with dichloromethane, washed with sodium bicarbonate and then with brine, the organic phase is dried and concentrated by evaporation. After column chromatography with hexane/ethyl acetate, 211 mg of product results.

[1H]-NMR (CDCl$_3$): 8 br 1H, 7.24 dd 1H, 6.95 m 2H, 6.88 br 2H, 6.7 br 1H, 4.62 q 1H, 4.44 s 2H, 4.32 s 2H, 1.55 m 9H plus 3H.

The following are produced in the same way:

6-((Thien-3-yl)-methyl-(tert-butyloxycarbonyl)aminomethyl)-2-methyl-1,4-benzoxazin-3-one 6-(benzyl-(tert-butyloxycarbonyl)aminomethyl)-2-methyl-1,4-benzoxazin-3-one 6-((4-methoxybenzyl)(tert-butyloxycarbonyl)aminomethyl)-2-methyl-1,4-benzoxazin-3-one 6-((3-chlorobenzyl)(tert-butyloxycarbonyl)aminomethyl)-2-methyl-1,4-benzoxazin-3-one 6-((2-chloro-6-fluorobenzyl)(tert-butyloxycarbonyl)aminomethyl)-2-methyl-1,4-benzoxazin-3-one 6-((4-chlorobenzyl)(tert-butyloxycarbonyl)aminomethyl)-2-methyl-1,4-benzoxazin-3-one 6-((3,4-dichlorobenzyl)(tert-butyloxycarbonyl)aminomethyl)-2-methyl-1,4-benzoxazin-3-one 6-((2-chlorobenzyl)(tert-butyloxycarbonyl)aminomethyl)-2-methyl-1,4-benzoxazin-3-one 6-((2,4-dichlorobenzyl)(tert-butyloxycarbonyl)aminomethyl)-2-methyl-1,4-benzoxazin-3-one 6-((2,3-dimethylbenzyl)(tert-butyloxycarbonyl)aminomethyl)-2-methyl-1,4-benzoxazin-3-one 6-((3-fluorobenzyl)(tert-butyloxycarbonyl)aminomethyl)-2-methyl-1,4-benzoxazin-3-one 6-((indan-1-yl)(tert-butyloxycarbonyl)aminomethyl)-2-methyl-1,4-benzoxazin-3-one  6-((indan-2-yl)(tert-butyloxycarbonyl)aminomethyl)-2-methyl-1,4-benzoxazin-3-one
6-((cyclohexylmethyl)(tert-butyloxycarbonyl)aminomethyl)-2-methyl-1,4-benzoxazin-3-one
6-((1,2,3,4-tetrahydronaphth-1-yl)(tert-butyloxycarbonyl)aminomethyl)-2-methyl-1,4-benzoxazin-3-one
6-((diphenylmethyl)(tert-butyloxycarbonyl)aminomethyl)-2-methyl-1,4-benzoxazin-3-one
6-((3-methoxybenzyl)(tert-butyloxycarbonyl)aminomethyl)-2-methyl-1,4-benzoxazin-3-one
6-((3-nitrobenzyl)(tert-butyloxycarbonyl)aminomethyl)-2-methyl-1,4-benzoxazin-3-one
6-((4-nitrobenzyl)(tert-butyloxycarbonyl)aminomethyl)-2-methyl-1,4-benzoxazin-3-one 6-((4-sulfamoylbenzyl)(tert-butyloxycarbonyl)aminomethyl)-2-methyl-1,4-benzoxazin-3-one
6-((4-methylsulfonylbenzyl)(tert-butyloxycarbonyl)aminomethyl)-2-methyl-1,4-benzoxazin-3-one
6-((4-fluorobenzyl)(tert-butyloxycarbonyl)aminomethyl)-2-methyl-1,4-benzoxazin-3-one
6-((4-dimethylaminobenzyl)(tert-butyloxycarbonyl)aminomethyl)-2-methyl-1,4-benzoxazin-3-one
6-((3,4-methylenedioxybenzyl)(tert-butyloxycarbonyl)aminomethyl)-2-methyl-1,4-benzoxazin-3-one
6-((2-fluorobenzyl)(tert-butyloxycarbonyl)aminomethyl)-2-methyl-1,4-benzoxazin-3-one
6-((4-methylbenzyl)(tert-butyloxycarbonyl)aminomethyl)-2-methyl-1,4-benzoxazin-3-one
6-((4-pyridyl)-methyl(tert-butyloxycarbonyl)aminomethyl)-2-methyl-1,4-benzoxazin-3-one
6-((3-pyridyl)-methyl(tert-butyloxycarbonyl)aminomethyl)-2-methyl-1,4-benzoxazin-3-one
6-((2-furyl)-methyl(tert-butyloxycarbonyl)aminomethyl)-2-methyl-1,4-benzoxazin-3-one
6-((naphth-1-yl)-methyl(tert-butyloxycarbonyl)aminomethyl)-2-methyl-1,4-benzoxazin-3-one
6-((3-trifluoromethylbenzyl)(tert-butyloxycarbonyl)-aminomethyl)-2-methyl-1,4-benzoxazin-3-one
6-(Benzyl(tert-butyloxycarbonyl)amino)-6,7-cyclopenteno-2-methyl-1,4-benzoxazin-3-one
6-(benzyl(tert-butyloxycarbonyl)amino)-6,7-cyclohexeno-2-methyl-1,4-benzoxazin-3-one
6-((Thien-2-yl)-methyl-(tert-butyloxycarbonyl)amino)-6,7-cyclopenteno-2-methyl-1,4-benzoxazin-3-one
6-((thien-2-yl)-methyl-(tert-butyloxycarbonyl)amino)-6,7-cyclohexeno-2-methyl-1,4-benzoxazin-3-one
6-(3-chlorobenzyl (tert-butyloxycarbonyl)amino)-6,7-cyclopenteno-2-methyl-1,4-benzoxazin-3-one
6-(3-chlorobenzyl(tert-butyloxycarbonyl)amino)-6,7-cyclohexeno-2-methyl-1,4-benzoxazin-3-one
7-(3-chlorobenzyl(tert-butyloxycarbonyl)amino)-6,7-cyclohexeno-2-methyl-1,4-benzoxazin-3-one
6-(2-(benzyl(tert-butyloxycarbonyl)amino)-prop-1-yl)-2-methyl-1,4-benzoxazin-3-one
6-(1-(benzyl(tert-butyloxycarbonyl)amino)-prop-1-yl)-2-methyl-1,4-benzoxazin-3-one
6-(1-((thien-2-yl)-methyl(tert-butyloxycarbonyl)-amino)-prop-1-yl)-2-methyl-1,4-benzoxazin-3-one
6-((Thien-2-yl)-methyl-(tert-butyloxycarbonyl)aminomethyl)-2-ethyl-1,4-benzoxazin-3-one
6-((thien-2-yl)-methyl-(tert-butyloxycarbonyl)aminomethyl)-2-propyl-1,4-benzoxazin-3-one 2-Methyl-3-oxo-6-[2-(3-chlorobenzyl-tert-butyloxycarbonylamino)-ethyl]-3,4-dihydro-2H-1,4-benzoxazine 550 mg (1.623 mmol) of 2-methyl-3-oxo-6-[2-(3-chlorobenzylamino)-ethyl]-3,4-dihydro-2H-1,4-benzoxazine is mixed in 10 ml of absolute dichloromethane with 425.2 mg of di-tert-butyldicarbonate and 243.3 mg of triethylamine. After three hours of stirring at room temperature, the batch is diluted with dichloromethane and then washed with saturated sodium bicarbonate solution and with brine. After the organic phase is dried, the solvent is spun off, and the remaining residue is chromatographed on silica gel (mobile solvent: ethyl acetate/hexane). The yield is 742.6 mg (>100%).

6-((Thien-2-yl)-methyl-(tert-butyloxycarbonyl)aminomethyl)-2-methyl-1,4-benzoxazine-3-thione 243 mg of Lawesson's reagent is added to 200 mg of 6-((thien-2-yl)-methyl(tert-butyloxycarbonyl)aminomethyl)-2-methyl-1,4-benzoxazin-3-one in 15 ml of dimethoxyethane at room temperature, and it is stirred for 4 more hours. After concentration by evaporation and after column chromatography with hexane/ethyl acetate, 151 mg of product results.

[1H]-NMR (CDCl$_3$): 9.4 br 1H, 6,7 to 7.3 6H, 5.01 q 1H, 4.5 s br 2H, 4.35 s br 2H, 1.5 s 9H, 1.6 d 3H. MS: 404 m/e (M$^+$).

The following are produced in the same way:
6-((Thien-3-yl)-methyl(tert-butyloxycarbonyl)aminomethyl)-2-methyl-1,4-benzoxazine-3-thione
6-(benzyl(tert-butyloxycarbonyl)aminomethyl)-2-methyl-1,4-benzoxazine-3-thione
6-((4-methoxybenzyl)(tert-butyloxycarbonyl)aminomethyl)-2-methyl-1,4-benzoxazine-3-thione
6-((3-chlorobenzyl)(tert-butyloxycarbonyl)aminomethyl)-2-methyl-1,4-benzoxazine-3-thione
6-((2-chloro-6-fluorobenzyl)(tert-butyloxycarbonyl)aminomethyl)-2-methyl-1,4-benzoxazine-3-thione
6-((4-chlorobenzyl)(tert-butyloxycarbonyl)aminomethyl)-2-methyl-1,4-benzoxazine-3-thione
6-((3,4-dichlorobenzyl)(tert-butyloxycarbonyl)aminomethyl)-2-methyl-1,4-benzoxazine-3-thione
6-((2-chlorobenzyl)(tert-butyloxycarbonyl)aminomethyl)-2-methyl-1,4-benzoxazine-3-thione
6-((2,4-dichlorobenzyl)(tert-butoxycarbonyl)aminomethyl)-2-methyl-1,4-benzoxazine-3-thione
6-((2,3-dimethylbenzyl)(tert-butyloxycarbonyl)aminomethyl)-2-methyl-1,4-benzoxazine-3-thione
6-((3-fluorobenzyl)(tert-butyloxycarbonyl)aminomethyl)-2-methyl-1,4-benzoxazine-3-thione
6-((indan-1-yl)(tert-butyloxycarbonyl)aminomethyl)-2-methyl-1,4-benzoxazine-3-thione
6-((indan-2-yl)(tert-butyloxycarbonyl)aminomethyl)-2-methyl-1,4-benzoxazine-3-thione
6-((cyclohexylmethyl)(tert-butyloxycarbonyl)aminomethyl)-2-methyl-1,4-benzoxazine-3-thione
6-((1,2,3,4-tetrahydronaphth-1-yl)(tert-butyloxycarbonyl)aminomethyl)-2-methyl-1,4-benzoxazine-3-thione
6-((diphenylmethyl)(tert-butyloxycarbonyl)aminomethyl)-2-methyl-1,4-benzoxazine-3-thione
6-((3-methoxybenzyl)(tert-butyloxycarbonyl)aminomethyl)-2-methyl-1,4-benzoxazine-3-thione
6-((3-nitrobenzyl)(tert-butyloxycarbonyl)aminomethyl)-2-methyl-1,4-benzoxazine-3-thione 6-((4-nitrobenzyl)(tert-butyloxycarbonyl)aminomethyl)-2-methyl-1,4-benzoxazine-3-thione 6-((4-sulfamoylbenzyl)(tert-butyloxycarbonyl)aminomethyl)-2-methyl-1,4-benzoxazine-3-thione 6-((4-methylsulfonylbenzyl)(tert-butyloxycarbonyl)aminomethyl)-2-methyl-1,4-benzoxazine-3-thione 6-((4-fluorobenzyl)(tert-butyloxycarbonyl)aminomethyl)-2-methyl-1,4-benzoxazine-3-thione 6-((4-dimethylaminobenzyl)(tert-butyloxycarbonyl)aminomethyl)-2-methyl-1,4-benzoxazine-3-thione 6-((3,4-methylenedioxybenzyl)(tert-butyloxycarbonyl)aminomethyl)-2-methyl-1,4-benzoxazine-3-thione 6-((2-fluorobenzyl)(tert-butyloxycarbonyl)aminomethyl)-2-methyl-1,4-benzoxazine-3-thione 6-((4-methylbenzyl)(tert-butyloxycarbonyl)aminomethyl)-2-methyl-1,4-benzoxazine-3-thione 6-((4-pyridyl)-methyl(tert-butyloxycarbonyl)aminomethyl)-2-methyl-1,4-benzoxazine-3-thione 6-((3-pyridyl)-methyl(tert-butyloxycarbonyl)aminomethyl)-2-methyl-1,4-benzoxazine-3-thione 6-((2-furyl)-methyl(tert-butyloxycarbonyl)aminomethyl)-2-methyl-1,4-benzoxazine-3-thione 6-((naphth-1-yl)-methyl(tert-butyloxycarbonyl)aminomethyl)-2-methyl-1,4-benzoxazine-3-thione 6-((3-trifluoromethylbenzyl)(tert-butyloxycarbonyl)aminomethyl)-2-methyl-1,4-benzoxazine-3-thione 6-(benzyl(tert-butyloxycarbonyl)amino)-6,7-cyclopenteno-2-methyl-1,4-benzoxazine-3-thione 6-(benzyl(tert-butyloxycarbonyl)amino)-6,7-cyclohexeno-2-methyl-1,4-benzoxazine-3-thione 6-((thien-2-yl)-methyl-(tert-butyloxycarbonyl)amino)-6,7-cyclopenteno-2-methyl-1,4-benzoxazine-3-thione 6-((thien-2-yl)-methyl-(tert-butyloxycarbonyl)amino)-6,7-cyclohexeno-2-methyl-1,4-benzoxazine-3-thione 6-(3-chlorobenzyl(tert-butyloxycarbonyl)amino)-6,7-cyclopenteno-2-methyl-1,4-benzoxazine-3-thione 6-(3-chlorobenzyl(tert-butyloxycarbonyl)amino)-6,7-cyclohexeno-2-methyl-1,4-benzoxazine-3-thione 7-(3-chlorobenzyl(tert-butyloxycarbonyl)amino)-6,7-cyclohexeno-2-methyl-1,4-benzoxazine-3-thione 6-(2-(benzyl(tert-butyloxycarbonyl)amino)-prop-1-yl)-2-methyl-1,4-benzoxazine-3-thione 6-(1-benzyl(tert-butyloxycarbonyl)amino)-prop-1-yl)-2-methyl-1,4-benzoxazine-3-thione 6-(1-((thien-2-yl)-methyl(tert-butyloxycarbonyl)amino)-prop-1-yl)-2-methyl-1,4-benzoxazine-3-thione 6-((thien-2-yl)-methyl-(tert-butyloxycarbonyl)aminomethyl)-2-ethyl-1,4-benzoxazine-3-thione 6-((thien-2-yl)-methyl-(tert-butyloxycarbonyl)aminomethyl)-2-propyl-1,4-benzoxazine-3-thione 2-Methyl-6-[2-(3-chlorobenzyl-tert-butyloxycarbonylamino)-ethyl]-3,4-dihydro-2H-1,4-benzoxazine-3-thione 730.6 mg (1.696 mmol) of 2-methyl-3-oxo-6-[2-(3-chlorobenzyl-tert-butyloxycarbonylamino)-ethyl]-3,4-dihydro-2H-1,4-benzoxazine is mixed in 8 ml of pyridine with 201.1 mg (0.607 mmol) of phosphorus pentasulfide, and then it is refluxed for four hours. The solvent is spun off, and the remaining residue is chromatographed on silica gel (mobile solvent: ethyl acetate/hexane). The yield is 439.3 mg (58%).

EXAMPLE 2

6-((Thien-2-yl)-methyl(tert-butyloxycarbonyl)aminomethyl)-3-amino-2-methyl-1,4-benzoxazine 148 mg of 6-((thien-2-yl)-methyl(tert-butyloxycarbonyl)amino-methyl)-2-methyl-1,4-benzoxazine-3-thione is stirred into 70 ml of saturated ammonia solution in methanol (commercially available). After 1 day at room temperature, the crude product is obtained after concentration by evaporation. Column chromatography with ethyl acetate purifies the product. A yield of 88% results.

[1H]-NMR (DMSO): 7.42 dd 1H, 6.99 d 2H, 6.7 m 3H, 4.64 q 1H, 4.45 s br 2H, 4.23 s br 2H, 1.49 s 9H, 1.28 d 3H. MS: 387 m/e (M+).

The following are produced in the same way:

6-((Thien-3-yl)-methyl(tert-butyloxycarbonyl)aminomethyl)-3-amino-2-methyl-1,4-benzoxazine 6-(Benzyl-(tert-butyloxycarbonyl)aminomethyl)-3-amino-2-methyl-1,4-benzoxazine

[1H]-NMR (MeOH): 7.07 to 7.23 m 5H, 6.75 1H, 6.64 2H, 4.61 q 1H, 4.3 s br 2H, 4.2 s br 2H, 1.41 s 9H, 1.26 d 3H.

6-((4-Methoxybenzyl)(tert-butyloxycarbonyl)aminomethyl)-3-amino-2-methyl-1,4-benzoxazine

[1H]-NMR (CDCl3): 7.2 m 2H, 6.9 to 6.75 m 4H, 4.62 q 1H, 4.2 to 4.4 m br 4H, 3.80 s 3H, 1.50 s 9H, 1.49 d 3H. MS: 411 m/e (M+).

6-((3-Chlorobenzyl)(tert-butyloxycarbonyl)aminomethyl)-3-amino-2-methyl-1,4-benzoxazine 6-((2-chloro-6-fluorobenzyl)(tert-butyloxycarbonyl)aminomethyl)-3-amino-2-methyl-1,4-benzoxazine 6-((4-chlorobenzyl)(tert-butyloxycarbonyl)aminomethyl)-3-amino-2-methyl-1,4-benzoxazine 6-((4-methylbenzyl)(tert-butyloxycarbonyl)aminomethyl)-3-amino-2-methyl-1,4-benzoxazine 6-((4-pyridyl)-methyl(tert-butyloxycarbonyl)aminomethyl)-3-amino-2-methyl-1,4-benzoxazine 6-((3-pyridyl)-methyl(tert-butyloxycarbonyl)aminomethyl)-3-amino-2-methyl-1,4-benzoxazine 6-((2-furyl)-methyl(tert-butyloxycarbonyl)aminomethyl)-3-amino-2-methyl-1,4-benzoxazine 6-((naphth-1-yl)-methyl(tert-butyloxycarbonyl)aminomethyl)-3-amino-2-methyl-1,4-benzoxazine 6-((3-trifluoromethylbenzyl)(tert-butyloxycarbonyl)aminomethyl)-3-amino-2-methyl-1,4-benzoxazine 6-((3,4-dichlorobenzyl)(tert-butyloxycarbonyl)aminomethyl)-3-amino-2-methyl-1,4-benzoxazine 6-((2-chlorobenzyl)(tert-butyloxycarbonyl)aminomethyl)-3-amino-2-methyl-1,4-benzoxazine 6-((2,4-dichlorobenzyl)(tert-butyloxycarbonyl)aminomethyl)-3-amino-2-methyl-1,4-benzoxazine 6-((2,3-dimethylbenzyl)(tert-butyloxycarbonyl)aminomethyl)-3-amino-2-methyl-1,4-benzoxazine 6-((3-fluorobenzyl)(tert-butyloxycarbonyl)aminomethyl)-3-amino-2-methyl-1,4-benzoxazine 6-((indan-1-yl)(tert-butyloxycarbonyl)aminomethyl)-3-amino-2-methyl-1,4-benzoxazine 6-((indan-2-yl)(tert-butyloxycarbonyl)aminomethyl)-3-amino-2-methyl-1,4-benzoxazine 6-((cyclohexylmethyl)(tert-butyloxycarbonyl)aminomethyl)-3-amino-2-methyl-1,4-benzoxazine 6-((1,2,3,4-tetrahydronaphth-1-yl)(tert-butyloxycarbonyl)aminomethyl)-3-amino-2-methyl-1,4-benzoxazine 6-((diphenylmethyl)(tert-butyloxycarbonyl)aminomethyl)-3-amino-2-methyl-1,4-benzoxazine 6-((3-methoxybenzyl)(tert-butyloxycarbonyl)aminomethyl)-3-amino-2-methyl-1,4-benzoxazine 6-((3-nitrobenzyl)(tert-butoxycarbonyl)aminomethyl)-3-amino-2-methyl-1,4-benzoxazine 6-((4-nitrobenzyl)(tert-butyloxycarbonyl)aminomethyl)-3-amino-2-methyl-1,4-benzoxazine 6-((4-sulfamoylbenzyl)(tert-butyloxycarbonyl)aminomethyl)-3-amino-2-methyl-1,4-benzoxazine 6-((4-methylsulfonylbenzyl)(tert-butyloxycarbonyl)aminomethyl)-3-amino-2-methyl-1,4-benzoxazine 6-((4-fluorobenzyl)(tert-butyloxycarbonyl)aminomethyl)-3-amino-2-methyl-1,4-benzoxazine 6-((4-dimethylaminobenzyl)(tert-butyloxycarbonyl)aminomethyl)-3-amino-2-methyl-1,4-benzoxazine 6-((3,4-methylenedioxybenzyl)(tert-butyloxycarbonyl)aminomethyl)-3-amino-2-methyl-1,4-benzoxazine 6-((2-fluorobenzyl)(tert-butyloxycarbonyl)aminomethyl)-3-amino-2-methyl-1,4-benzoxazine From 6-((4-nitrobenzyl)(tert-butyloxycarbonyl)aminomethyl)-2-methyl-1,4-benzoxazine-3-thione after reduction 6-((4-aminobenzyl)(tert-butyloxycarbonyl)aminomethyl)-3-amino-2-methyl-1,4-benzoxazine 6-(Benzyl(tert-butyloxycarbonyl)amino)-6,7-cyclopenteno-3-amino-2-methyl-1,4-benzoxazine

[1H]-NMR (DMSO): 7.1 to 7.33 m 4H, 6.4 to 6,7 m 3H, 4.6 q 1H, 4.45 s br 2H, 4.0 s br 1H, 2.7 m 2H, 2.3 m 1H, 1.8 m 1H, 1.33 s 9H, 1.24 d 3H.

6-(Benzyl(tert-butyloxycarbonyl)amino)-6,7-cyclohexeno-3-amino-2-methyl-1,4-benzoxazine

[1H]-NMR (MeOH): 7.05 to 7.21 m 5H, 6.6 s 1H, 6.42 d 1H, 4.55 q 1H, 4.5 s br 4H, 2.5 m 2H, 1.8 m 2H, 1.6 m 2H, 1.27 m 12H.

6-((Thien-2-yl)-methyl-(tert-butyloxycarbonyl)amino)-6,7-cyclopenteno-3-amino-2-methyl-1,4-benzoxazine 6-((thien-2-yl)-methyl-(tert-butyloxycarbonyl)amino)-6,7-cyclohexeno-3-amino-2-methyl-1,4-benzoxazine 6-(3-chlorobenzyl-(tert-butyloxycarbonyl)amino)-6,7-cyclopenteno-3-amino-2-methyl-1,4-benzoxazine 6-(3-chlorobenzyl-(tert-butyloxycarbonyl)amino)-6,7-cyclohexeno-3-amino-2-methyl-1,4-benzoxazine 7-(3-chlorobenzyl-(tert-butyloxycarbonyl)amino)-6,7-cyclohexeno-3-amino-2-methyl-1,4-benzoxazine 6-(2-(benzyl-(tert-butyloxycarbonyl)amino)-prop-1-yl)-3-amino-2-methyl-1,4-benzoxazine 6-(1-(benzyl(tert-butyloxycarbonyl)amino)-prop-1-yl)-3-amino-2-methyl-1,4-benzoxazine

[1H]-NMR (DMSO): 6.6 to 7.2 m 10H, 5.0 m 1H, 4.63q 1H, 4.05 to 4.3 m br 2H, 1.8 dq br 2H, 1.39 s 9H, 1.25 d 3H, 0.81 tr 3H.

6-(1-((Thien-2-yl)-methyl(tert-butyloxycarbonyl)amino)-prop-1-yl)-3-amino-2-methyl-1,4-benzoxazine 6-((thien-2-yl)-methyl-(tert-butyloxycarbonyl)aminomethyl)-3-amino-2-ethyl-1,4-benzoxazine 6-((thien-2-yl)-methyl-(tert-butyloxycarbonyl)aminomethyl)-3-amino-2-propyl-1,4-benzoxazine 2-methyl-3-amino-6-[2-(3-chlorobenzyl-tert-butyloxycarbonylamino)-ethyl]-2H-1,4-benzoxazine 430 mg (0.962 mmol) of 2-methyl-6-[2-(3-chlorobenzyl-tert-butyloxycarbonylamino)-ethyl]-3,4-dihydro-2H-1,4-benzoxazine-3-thione is mixed with 10 ml of a solution of ammonia in methanol (7N) and stirred overnight at room temperature. The solvent is spun off, and the residue is chromatographed on silica gel (mobile solvent: dichloromethane/isopropanol). The yield is 218.6 mg (52.9%).

EXAMPLE 3

6-((Thien-2-yl)-methylaminomethyl)-3-amino-2-methyl-1,4-benzoxazine dihydrochloride 28 mg of 6-((thien-2-yl)-methyl(tert-butyloxycarbonyl)aminomethyl)-3-amino-2-methyl-1,4-benzoxazine is stirred in 2 ml of dioxane with 0.6 ml of 4N hydrochloric acid. After 12 hours, it is diluted with some ethyl acetate, the crystals are suctioned off, washed with a little ethyl acetate and dried in a vacuum. 20.4 mg of product (a yield of 79%) is obtained.

[1H]-NMR (DMSO): 9.8 broad, 7.63 dd 1H, 7.45 d 1H, 7.37 d 1H, 7.32 dd 1H, 7.11 m 2H, 5.37 q 1H, 4.4 br 2H, 4.13 br 2H, 1.51 d 3H.

The following are produced in the same way:

6-((Thien-3-yl)-methylaminomethyl)-3-amino-2-methyl-1,4-benzoxazine dihydrochloride 6-(benzylaminomethyl)-3-amino-2-methyl-1,4-benzoxazine dihydrochloride 6-((4-methoxybenzyl)aminomethyl)-3-amino-2-methyl-1,4-benzoxazine dihydrochloride

[1H]-NMR (DMSO): 9.65 broad, 7.51 m 2H, 7.49 d 1H, 7.34 dd 1H, 7.11 d 1H, 7.0 m 2H, 5.35 q 1H, 4.1 br 4H, 3.8 s 3H, 1.51 d 3H.

6-((3-Chlorobenzyl)aminomethyl)-3-amino-2-methyl-1,4-benzoxazine dihydrochloride 6-((2-chloro-6-fluorobenzyl)aminomethyl)-3-amino-2-methyl-1,4-benzoxazine dihydrochloride 6-((4-chlorobenzyl)aminomethyl)-3-amino-2-methyl-1,4-benzoxazine dihydrochloride 6-((4-methylbenzyl)aminomethyl)-3-amino-2-methyl-1,4-benzoxazine dihydrochloride 6-((4-pyridyl)-methylaminomethyl)-3-amino-2-methyl-1,4-benzoxazine dihydrochloride

[1H]-NMR (DMSO): 9.6 broad, 8.83 br 2H, 8.05 br 2H, 7.1 to 7.55 m 3H, 5.40 q 1H, 4.39 s br 2H, 4.2 s br 2H, 1.51 d 3H.

6-((3-Pyridyl)-methylaminomethyl)-3-amino-2-methyl-1,4-benzoxazine dihydrochloride 6-((2-furyl)-methylaminomethyl)-3-amino-2-methyl-1,4-benzoxazine dihydrochloride 6-((naphth-1-yl)-methylaminomethyl)-3-amino-2-methyl-1,4-benzoxazine dihydrochloride 6-((3-trifluoromethylbenzyl)aminomethyl)-3-amino-2-methyl-1,4-benzoxazine dihydrochloride 6-((3,4-dichlorobenzyl)aminomethyl)-3-amino-2-methyl-1,4-benzoxazine dihydrochloride 6-((2-chlorobenzyl)aminomethyl)-3-amino-2-methyl-1,4-benzoxazine dihydrochloride 6-((2,4-dichlorobenzyl)aminomethyl)-3-amino-2-methyl-1,4-benzoxazine dihydrochloride 6-((2,3-dimethylbenzyl)aminomethyl)-3-amino-2-methyl-1,4-benzoxazine dihydrochloride 6-((3-fluorobenzyl)aminomethyl)-3-amino-2-methyl-1,4-benzoxazine dihydrochloride 6-((indan-1-yl)aminomethyl)-3-amino-2-methyl-1,4-benzoxazine dihydrochloride 6-((indan-2-yl)aminomethyl)-3-amino-2-methyl-1,4-benzoxazine dihydrochloride 6-((cyclohexylmethyl)aminomethyl)-3-amino-2-methyl-1,4-benzoxazine dihydrochloride 6-((1,2,3,4-tetrahydronaphth-1-yl)aminomethyl)-3-amino-2-methyl-1,4-benzoxazine dihydrochloride 6-((diphenylmethyl)aminomethyl)-3-amino-2-methyl-1,4-benzoxazine dihydrochloride 6-((3-methoxybenzyl)aminomethyl)-3-amino-2-methyl-1,4-benzoxazine dihydrochloride 6-((3-nitrobenzyl)aminomethyl)-3-amino-2-methyl-1,4-benzoxazine dihydrochloride 6-((4-nitrobenzyl)aminomethyl)-3-amino-2-methyl-1,4-benzoxazine dihydrochloride 6-((4-sulfamoylbenzyl)aminomethyl)-3-amino-2-methyl-1,4-benzoxazine dihydrochloride 6-((4-methylsulfonylbenzyl)aminomethyl)-3-amino-2-methyl-1,4-benzoxazine dihydrochloride 6-((4-fluorobenzyl)aminomethyl)-3-amino-2-methyl-1,4-benzoxazine dihydrochloride 6-((4-dimethylaminobenzyl)aminomethyl)-3-amino-2-methyl-1,4-benzoxazine trihydrochloride 6-((3,4-methylenedioxybenzyl)aminomethyl)-3-amino-2-methyl-1,4-benzoxazine dihydrochloride 6-((2-fluorobenzyl)aminomethyl)-3-amino-2-methyl-1,4-benzoxazine dihydrochloride 6-((4-aminobenzyl)aminomethyl)-3-amino-2-methyl-1,4-benzoxazine trihydrochloride 6-(Benzylamino)-6,7-cyclopenteno-3-amino-2-methyl-1,4-benzoxazine dihydrochloride

[1H]-NMR (MeOH): 7.4 m 6H, 7.00 s 1H, 5.12 q 1H, 4.2 s br 2H, 4.9 1H, 3.2, 3.0, 2.65 m 1H 1.47 d 3H and 2.4 m 1H 1.47 d 3H.

6-(Benzylamino)-6,7-cyclohexeno-3-amino-2-methyl-1,4-benzoxazine dihydrochloride

[1H]-NMR (DMSO): 9.5 broad, 7.67 m 2H, 7.45 m 4H, 6.92s 1H, 5.31 q 1H, 4.44 br 1H, 4.21 br 2H, 2.77 ABq 2H, 1.7 to 2.3 m 4H, 1.49 d 3H.

6-((Thien-2-yl)-methylamino)-6,7-cyclopenteno-3-amino-2-methyl-1,4-benzoxazine dihydrochloride

[1H]-NMR (DMSO): 9.6 broad, 7.67 m 2H, 7.43 dd 1H, 7.13 dd 1H, 7.97 s 1H, 5.32 q 1H, 4.75 br 1H, 4.4 br 1H, 3.2 m 1H, 2.9 m 1H, 2.32 to 2.5 m 2H, 1.5 d 3H.

6-((Thien-2-yl)-methylamino)-6,7-cyclohexeno-3-amino-2-methyl-1,4-benzoxazine dihydrochloride

[1H]-NMR (DMSO): 9.5 broad, 7.65 d 1H, 7.45 d 1H, 7.41 s 1H, 7.13 dd 1H, 6.91 s 1H, 5.30 q 1H, 4.47 br 2H, 4.43 br 1H, 2.75 m 2H, 2.2 m 2H, 1.8 m 2H, 1.49 d 3H.

6-(3-Chlorobenzylamino)-6,7-cyclopenteno-3-amino-2-methyl-1,4-benzoxazine dihydrochloride 6-(3-chlorobenzylamino)-6,7-cyclohexeno-3-amino-2-methyl-1,4-benzoxazine dihydrochloride 6-(2-(benzylamino)-prop-1-yl)-3-amino-2-methyl-1,4-benzoxazine dihydrochloride 7-(3-chlorobenzylamino)-6,7-cyclohexeno-3-amino-2-methyl-1,4-benzoxazine dihydrochloride 6-(1-(benzylamino)-prop-1-yl)-3-amino-2-methyl-1,4-benzoxazine dihydrochloride 6-(1-((thien-2-yl)-methylamino)-prop-1-yl)-3-amino-2-methyl-1,4-benzoxazine dihydrochloride 6-((thien-2-yl)-methyl-aminomethyl)-3-amino-2-ethyl-1,4-benzoxazine dihydrochloride 6-((thien-2-yl)-methyl-aminomethyl)-3-amino-2-propyl-1,4-benzoxazine dihydrochloride 2-Methyl-3-amino-6-[2-(3-chlorobenzylamino)-ethyl]-2H-1,4-benzoxazine dihydrochloride 203.9 mg (0.474 mmol) of 2-methyl-3-amino-6-[2-(3-chlorobenzyl-tert-butyloxycarbonylamino)-ethyl]-2H-1,4-benzoxazine is mixed with 7 ml of an HCl in dioxane solution (4M) and stirred for three hours at room temperature. The precipitated product is suctioned off, and washed with toluene and with dichloromethane. After drying on the oil pump, 163.3 mg (85.5%) of the desired product is obtained as dihydrochloride.

EXAMPLE 4 a) 4-Hydroxy-3-amino-benzoic acid methyl ester 25 g (126.8 mmol) of 3-nitro-4-hydroxybenzoic acid methyl ester is dissolved in a mixture of 1120 ml of ethanol and 460 ml of THF. After 104.7 g (1.6 mol) of zinc dust and 31.7 g (592.5 mmol) of ammonium chloride, dissolved in 215 ml of water, are added, the batch is stirred for 1¼ hours at room temperature. The reaction mixture is suctioned off via a glass fiber filter and washed with ample ethyl acetate. After the filtrate is spun in up to the dry state, the residue is taken up in 1500 ml of ethyl acetate, and the organic phase is washed twice with 150 ml of brine each. After the solvent is dried on sodium sulfate and spun off, 28.1 g of crude product remains. 26.5 g is obtained from a second batch of equal size.

Both crude products are put on a column together on silica gel (hexane/ethyl acetate as eluant).

The yield of 4-hydroxy-3-amino-benzoic acid methyl ester is 31.3 g (73.9%), melting point 141–149° C.

b) (±)-2-Methyl-3-oxo-6-(methoxycarbonyl)-3,4-dihydro-2H-1,4-benzoxazine 3.71 g (154.6 mmol) of sodium hydride (in the form of a 60% suspension) is suspended in 340 ml of dimethylformamide. At 0° C., 15.5 g (92.7 mmol) of 4-hydroxy-3-amino-benzoic acid-methyl ester, dissolved in 170 ml of dimethylformamide, is added in drops within 25 minutes to this suspension. After one hour of stirring at room temperature, 135 ml of tetrahydrofuran is added and again at 0° C., 16.78 g (92.6 mmol) of (±)-2-bromopropionic acid ethyl ester, dissolved in 340 ml of dimethylformamide, is added in drops within 10 minutes. Then, it is stirred for 15 hours at room temperature and for 2 hours at 40–45° C. Although starting material is present, it is worked up. The reaction mixture is carefully mixed with 25 ml of water, stirring is continued briefly, and then the mixture is evaporated to the dry state. A second batch with identical amounts used was implemented. The residues of both batches are taken up in ethyl acetate. In this case, a portion of the product precipitates, which is suctioned off. The filtrate is again spun in and treated with a little ethyl acetate. Product again precipitates. Then, the filtrate is chromatographed on silica gel (hexane/ethyl acetate as mobile solvent).

The total yield of (±)-2-methyl-3-oxo-6-(methoxycarbonyl)-3,4-dihydro-2H-1,4-benzoxazine-6-carboxylic acid methyl ester is 19.33 g (50.8%), melting point 164–167° C.

c) (±)-2-Methyl-3-oxo-6-hydroxymethyl-3,4-dihydro-2H-1,4-benzoxazine 10.3 g (46.6 mmol) of (±)-2-methyl-3-oxo-6-(methoxycarbonyl)-3,4-dihydro-2H-1,4-benzoxazine is dissolved in 164 ml of tetrahydrofuran. After 330 ml of toluene is added, the solution is cooled to −15° C. At this temperature, 144.2 ml of a 20% DIBAH solution in toluene is added in drops within 30 minutes. A color change from yellow to orange takes place. After 45 minutes of stirring at −15° C., 31 ml of isopropanol is added in drops at this temperature, and 68 ml of water is added in drops at 0° C. After 2½ hours of vigorous stirring at room temperature, the precipitate that is produced is suctioned off, washed with tetrahydrofuran, and the filtrate is spun in. The residue is chromatographed on silica gel (mobile solvent: methylene chloride/ethanol).

Generally, 5.09 g (56.6%) of the desired alcohol is obtained, melting point 149–154° C.

33 d) (±)-2-Methyl-3-oxo-6-chloromethyl-3,4-dihydro-2H-1,4-benzoxazine 4.59 g (23.8 mmol) of (±)-2-methyl-3-oxo-6-hydroxymethyl-3,4-dihydro-2H-1,4-benzoxazine is mixed with 5.53 g (54.6 mmol) of triethylamine after being dissolved in 900 ml of methylene chloride. At 0° C., 4.08 g (35.6 mmol) of methanesulfonic acid chloride is added in drops, and the batch is then stirred at room temperature for 5 hours. Another 3.8 ml of triethylamine and 1.4 ml of methanesulfonic acid chloride are added and stirred again for 20 hours at room temperature. A portion of methylene chloride (600 ml) is spun off. After dilution with 1 l of diethyl ether, the organic phase is washed twice with 50 ml of water each, once with 50 ml of saturated sodium bicarbonate solution and again with 50 ml of water. The organic phase is spun in after drying, and the residue is chromatographed on silica gel (mobile solvent: methylene chloride/ethanol). 2.95 g (58.7%) of the desired product in addition to 1.1 g (16.6%) of the corresponding mesylate are obtained, melting point 162–169° C.

e) (±)-2-Methyl-3-oxo-6-[(1-imidazolyl)-methyl]-3,4-dihydro-2H-1,4-benzoxazine 1.25 g (5.9 mmol) of (±)-2-methyl-3-oxo-6-chloromethyl-3,4-dihydro-2H-1,4-benzoxazine is dissolved in 12.5 ml of dimethyl sulfoxide, mixed with 0.804 g (11.8 mmol) of imidazole and stirred for 8 hours at 70° C. After stirring overnight at room temperature, the reaction mixture is spun on an oil pump until dry, and the residue is chromatographed on silica gel (mobile solvent: methylene chloride/ethanol). 940 mg (65.7%) of the desired imidazole compound is obtained, melting point 219–222° C.

f) (±)-2-Methyl-3-thioxo-6-[(1-imidazolyl)-methyl]-3,4-dihydro-2H-1,4-benzoxazine 390 mg (1.603 mmol) of (±)-2-methyl-3-oxo-6-[(1-imidazolyl)-methyl]-3,4-dihydro-2H-1,4-benzoxazine is dissolved in 42 ml of dimethoxyethane, mixed with 1.297 g (3.206 mmol) of Lawesson's reagent and stirred for 46 hours at room temperature. After the solvent is spun in, the residue is chromatographed on silica gel (mobile solvent: methylene chloride/ethanol). The fractions that are obtained by chromatography are removed from the polar contaminants by shaking with saturated sodium bicarbonate solution. 238.5 mg (57%) of the desired product is isolated, ting point 206–210° C.

g) (±)-2-Methyl-3-amino-6-[(1-imidazolyl)-methyl]-3,4-dihydro-1,4-benzoxazine 155 mg (0.597 mmol of (±)-2-methyl-3-thioxo-6-[(1-imidazolyl)-methyl]-3,4-dihydro-2H-1,4-benzoxazine is mixed with 10 ml of 7N $NH_3$ in methanol, and it is stirred for 2.5 hours at room temperature. After 20 ml of toluene is added, the solvent is then spun off, and the desired compound is obtained quantitatively, melting point 152–156° C.

What is claimed is:

1. A compound of formulae Ia and/or Ib, including tautomeric or isomeric forms or salts:

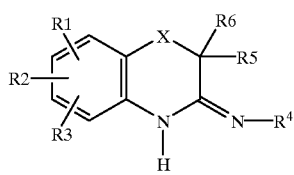

Ia

34

-continued

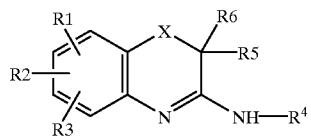

Ib in which

X means O or S, $R^1$ means $NO_2$, cyano, $CF_3$, —$OCF_3$, —$SO_2NR^7R^8$, —$CONR^7R^8$, —$NR^9$—$C(=NR^{10})$—$R^{11}$, —NH—CS—$NR^7R^8$, —NH—CO—$NR^7R^8$, $NR^{12}R^{13}$, or —CO—$R^{14}$; or $C_{6-10}$ aryl which optionally is substituted with halogen, cyano $C_{1-4}$ alkyl, —S—$R^9$, —$OR^9$, —$NR^7R^8$ or $CONR^7R^8$; or a 5- or 6-membered heteroaryl ring with 1 to 4 heteroatoms selected from oxygen, nitrogen or sulfur, which optionally is substituted with —$OR^9$, —$SR^9$, halogen, $C_{1-4}$-alkyl, $NR^7R^8$ or $CONR^7R^8$; or $C_{1-6}$ alkyl which is substituted with halogen, —$OR^9$, —$SR^9$, —$NR^7R^8$, —$NR^7R^{8'}$, =$NR^7$, =$NOC_{1-6}$ alkyl, =N-NHaryl, phenyl, $C_{3-7}$ cycloalkyl or 5- or 6-membered heteroaryl; or $C_{2-6}$ alkenyl which is substituted with halogen, $CONH_2$, C/N or phenyl; or $C_{2-6}$ alkynyl, which is substituted with halogen, $CONH_2$, C/N or phenyl; or $C_{3-7}$ cycloalkyl, $R^2$ means hydrogen or $R^1$ and $R^2$ together with two adjacent carbon atoms form a 5-, 6-, 7- or 8-membered ring, which is monocyclic or bicyclic, saturated or unsaturated, and which is optionally substituted with —$NR^7R^8$, —$NR^7R^{8'}$ or $C_{1-4}$ alkyl, $R^3$ means hydrogen, halogen, —S—$R^9$ or —O—$R^9$ or, independently has one of meanings of $R^1$, $R^4$ means hydrogen or acyl, $R^5$ means hydrogen, $R^6$ means $C_{3-7}$ cycloalkyl, $C_{6-10}$ aryl, $C_{1-6}$ alkyl, $C_{2-6}$ alkenyl or $C_{2-6}$ alkynyl radicals, which are each optionally substituted with halogen, OH, O—$C_{1-6}$ alkyl, SH, S—$C_{1-6}$ alkyl, $NR^{15}R^{16}$, 5- or 6-membered heteroaryl with 1–3 N, O or S atoms, phenyl or $C_{3-7}$ cycloalkyl, $R^7$ and $R^8$ mean hydrogen, $C_{1-6}$ alkyl, phenyl optionally substituted with halogen or $C_{1-4}$ alkyl, benzyl optionally substituted with halogen or $C_{1-4}$ alkyl or $C_{3-7}$ cycloalkyl, $R^{7'}$ means hydrogen, $C_{1-6}$ alkyl optionally substituted with OH, phenyl, cyano, COO—$C_{1-4}$ alkyl or carbonyl, $R^{8'}$ means $C_{1-6}$ alkyl, which is substituted with $C_{3-7}$ cycloalkyl, indanyl, $C_{6-10}$ aryl or 5- or 6-membered heteroaryl with 1–3 nitrogen, oxygen or sulfur atoms, whereby the aryl and heteroaryl radicals are optionally substituted with halogen, $C_{1-4}$ alkyl, $C_{1-4}$ alkoxy, $CF_3$, $NO_2$, $NH_2$, $N(C_{1-4}$ alkyl$)_2$, $SO_2CH_3$, —O—$CH_2$—O, $SO_2NH_2$, OH or COO—$C_{1-4}$ alkyl or indanyl or 1,2,3,4-tetrahydronaphthyl, or $R^{7'}$ and $R^{8'}$ together with the nitrogen atom form a 5- to 7-membered saturated heterocycle, which optionally contains another oxygen, nitrogen or sulfur atom and is optionally substituted with $C_{1-4}$ alkyl, phenyl, benzyl or benzoyl or forms an unsaturated 5-membered heterocycle, which contains a further 1–3 N atoms and is optionally substituted with phenyl, $C_{1-4}$ alkyl, halogen or $CH_2$—OH, $R^9$, $R^{10}$ and $R^{15}$, $R^{16}$ mean hydrogen or $C_{1-6}$ alkyl, $R^{11}$ means $C_{1-6}$ alkyl, —$NH_2$, —NH—$CH_3$, —NH—CN, $C_{6-10}$ aryl optionally substituted with halogen, $C_{1-4}$ alkyl or $CF_3$, or 5- or 6-membered heteroaryl with 1 to 4 nitrogen, sulfur or oxygen atoms that is optionally substituted with halogen, $C_{1-4}$ alkyl or $CF_3$, m means 0, 1 or 2, $R^{12}$, $R^{13}$ together with the nitrogen atom form a saturated 5-, 6- or 7-membered ring, which optionally contains another nitrogen, oxygen or sulfur atom and is optionally substituted with $C_{1-4}$ alkyl, phenyl, benzyl or benzoyl, and $R^{14}$ means hydrogen, phenyl, $C_{1-6}$ alkyl optionally substituted with $CO_2H$, $CO_2$—$C_{1-6}$ alkyl, hydroxy, $C_{1-4}$ alkoxy, halogen, $NR^7R^8$, $NR^{12}R^{13}$, $CONR^7R^8$ or phenyl, or $C_{2-6}$ alkenyl optionally substituted with phenyl, cyano, $CONR^7R^8$ or $CO_2C_{1-4}$ alkyl.

2. A compound according to claim 1, which contains an —$NR^7R^{8'}$ group as part of $R^1$ or $R^1$ and $R^2$ together, in which $R^{8'}$ means $C_{1-6}$ alkyl, which is substituted with $C_{3-7}$ cycloalkyl, indanyl, $C_{6-10}$ aryl or 5- or 6-membered heteroaryl with 1–3 nitrogen, oxygen or sulfur atoms, whereby the aryl and heteroaryl radicals are optionally substituted with halogen, $C_{1-4}$ alkyl, $C_{1-4}$ alkoxy, $CF_3$, $NO_2$, —O—$CH_2$—O, $SO_2NH_2$, OH or COO—$C_{1-4}$ alkyl.

3. A compound according to claim 1, wherein $R^1$ means $NO_2$, cyano, $CF_3$, —$OCF_3$, —$SO_2NR^7R^8$, —$CONR^7R^8$, —$NR^9$—C(=$NR^{10}$)—$R^{11}$, —NH—CS—$NR^7R^8$, —NH—CO—$NR^7R^8$, $NR^{12}R^{13}$ or —CO—$R^{14}$; or $C_{6-10}$ aryl, which optionally is substituted with halogen, cyano $C_{1-4}$ alkyl, —S—$R^9$, —O—$R^9$, —$NR^7R^8$ or $CONR^7R^8$; or 5- or 6-membered heteroaryl with 1 to 4 heteroatoms, selected from oxygen, nitrogen or sulfur, which optionally is substituted with —$OR^9$, —$SR^9$, halogen, $C_{1-4}$ alkyl, $NR^7R^8$ or $CONR^7R^8$; or $C_{1-6}$ alkyl which is substituted with halogen, —$OR^9$, —$SR^9$, —$NR^7R^8$, =$NR^7$, =$NOC_{1-6}$ alkyl, =N-NHaryl, phenyl, $C_{3-7}$ cycloalkyl or 5- or 6-membered heteroaryl; or $C_{2-6}$ alkenyl which is optionally substituted with halogen or phenyl; or $C_{2-6}$ alkynyl which optionally is substituted with halogen or phenyl; or $C_{3-7}$ cycloalkyl; and $R^2$ means hydrogen or $R^1$ and $R^2$ together with two adjacent carbon atoms form a 5-, 6-, or 7-membered ring, which is monocyclic or bicyclic, saturated or unsaturated, and which is optionally substituted in one to four places with $NR^7R^8$ or $C_{1-4}$ alkyl.

4. A compound of claim 1, wherein:

$R^1$ means $C_{1-6}$ alkyl, which is substituted with $NR^{7'}R^{8'}$, $R^2$ means hydrogen or $R^1$ and $R^2$ together with two adjacent carbon atoms form a 5-, 6-, 7- or 8-membered ring, which is monocyclic or bicyclic, saturated or unsaturated, and which is optionally substituted with —$NR^{7'}R^{8'}$, $R^3$ means hydrogen, halogen, $NO_2$, cyano, $CF_3$, —$OCF_3$, —$SO_2NR^7R^8$, $CONR^7R^8$, —$NR^9$—C(=$NR^{10}$)—$R^{11}$, —NH—CS—$NR^7R^8$, —NH—CO—$NR^7R^8$, $NR^{12}R^{13}$ or —CO—$R^{14}$, or $C_{6-10}$ aryl which optionally is substituted with halogen, cyano, $C_{1-4}$ alkyl, —S—$R^9$, —O—$R^9$, —$NR^7R^8$ or $CONR^7R^8$, or 5- or 6-membered heteroaryl with 1 to 4 heteroatoms selected from oxygen, nitrogen or sulfur, which optionally is substituted with —$OR^9$, —$SR^9$, halogen, $C_{1-4}$ alkyl, $NR^7R^8$ or $CONR^7R^8$, or $C_{1-6}$ alkyl which is substituted with halogen, —OR, —$SR^9$, —$NR^7R^8$, =$NR^7$, =$NOC_{1-6}$ alkyl, =N—NHaryl, phenyl, $C_{3-7}$ cycloalkyl, or 5- or 6-membered heteroaryl, or $C_{2-6}$ alkenyl which optionally is substituted with halogen or phenyl, or $C_{2-6}$ alkynyl which optionally is substituted with halogen or phenyl, $R^{8'}$ means $C_{1-6}$ alkyl which is substituted with $C_{3-7}$ cycloalkyl, indanyl, $C_{6-10}$ aryl or 5- or 6-membered heteroaryl with 1–3 nitrogen, oxygen or sulfur atoms, whereby the aryl and heteroaryl radicals are optionally substituted with halogen, $C_{1-4}$ alkyl, $C_{1-4}$ alkoxy, $CF_3$, $NO_2$, —O—$CH_2$—O, $SO_2NH_2$, OH or COO—$C_{1-4}$ alkyl, or $R^{7'}$ and $R^{8'}$ together with the nitrogen atom form a 5- to 7-membered saturated heterocycle, which optionally contains another oxygen, nitrogen or sulfur atom and is optionally substituted with $C_{1-4}$ alkyl, phenyl, benzyl or benzoyl or forms an unsaturated 5-membered heterocycle with 1–3 N atoms and optionally substituted with phenyl, $C_{1-4}$ alkyl, halogen or $CH_2$—OH.

5. A compound according to claim 1, in which $R^1$ and $R^2$ together with 2 adjacent carbon atoms is a saturated or unsaturated $C_{3-8}$ alkylene, in which the alkylene radical optionally contains a slightly condensed benzene radical which is optionally substituted by $NR^7R^8$, $NR^7R^{8'}$ or $C_{1-4}$ alkyl.

6. A compound according to claim 1, in which $R^1$ means $C_{1-6}$ alkyl which is substituted with $NR^7R^8$ or $NR^7R^{8'}$.

7. A compound of claim 1, which is:

6-phenyl-2-methyl-3-amino-1,4-benzoxazine;

4H-naphth[2,3-b]-2-methyl-3-amino-1,4-oxazine;

4H-naphth[1,2-b]-2-ethyl-3-amino-1,4-oxazine;

6,7-cyclopenteno-2-methyl-3-amino-1,4-benzoxazine;

6,7-cyclopenteno-2-ethyl-3-amino-1,4-benzoxazine;

5,6-cyclopenteno-2-methyl-3-amino-1,4-benzoxazine;

5,6-cyclopenteno-2-ethyl-3-amino-1,4-benzoxazine;

6,7-(methylenedioxy)-2-methyl-3-amino-1,4-benzoxazine;

6,7-(methylenedioxy)-2-ethyl-3-amino-1,4-benzoxazine;

6-cyclohexyl-2-methyl-3-amino-1,4-benzoxazine;

7-(1-morpholinyl)-2-methyl-3-amino-1,4-benzoxazine;

2-ethyl-3-amino-6,7,8,9-tetrahydro-napht[2,3-b]-1,4-oxazine;

2-methyl-3-amino-6,7,8,9-tetrahydro-napht[2,3-b]-1,4-oxazine;

3-methyl-2-amino-6,7,8,9-tetrahydro-napth[2,1-b]-1,4-oxazine;

3-ethyl-2-amino-6,7,8,9-tetrahydro-napht[2,1-b]-1,4-oxazine;

2-methyl-3-amino-6,7,8,9-tetrahydro-napht[2,3-b]-1,4-thiazine;

2-ethyl-3-amino-6,7,8,9-tetrahydro-napht[2,3-b]-1,4-thiazine;

6,7-cyclopenteno-2-methyl-3-amino-1,4-benzothiazine; or

N-[(2-methyl-1,4-benzoxazin-3-amino-7-yl]-(2-thienyl)-carboximidamide.

8. A compound of claim 1, which is:
6-((thien-2-yl)-methylaminomethyl)-3-amino-2-methyl-1,4-benzoxazine dihydrochloride;
6-((4-methoxybenzyl)aminomethyl)-3-amino-2-methyl-1,4-benzoxazine dihydrochloride;
6-((3-chlorobenzyl)aminomethyl)-3-amino-2-methyl-1,4-benzoxazine dihydrochloride;
6-((4-chlorobenzyl)aminomethyl)-3-amino-2-methyl-1,4-benzoxazine dihydrochloride;
6-((4-pyridyl)-methylaminomethyl)-3-amino-2-methyl-1,4-benzoxazine dihydrochloride;
6-(benzylamino)-6,7-cyclopenteno-3-amino-2-methyl-1,4-benzoxazine dihydrochloride;
6-(benzylamino)-6,7-cyclohexeno-3-amino-2-methyl-1,4-benzoxazine dihydrochloride;
6-((thien-2-yl)-methylamino)-6,7-cyclohexeno-3-amino-2-methyl-1,4-benzoxazine dihydrochloride;
6-((thien-2-yl)-methylamino)-6,7-cyclopenteno-3-amino-2-methyl-1,4-benzoxazine dihydrochloride;
6-(3-chlorobenzylamino)-6,7-cyclopenteno-3-amino-2-methyl-1,4-benzoxazine dihydrochloride;
6-(3-chlorobenzylamino)-6,7-cyclohexeno-3-amino-2-methyl-1,4-benzoxazine dihydrochloride;
6-(2-(benzylamino)-prop-1-yl)-3-amino-2-methyl-1,4-benzoxazine dihydrochloride;
7-(3-chlorobenzylamino)-6,7-cyclohexeno-3-amino-2-methyl-1,4-benzoxazine dihydrochloride;
6-((3,4-dichlorobenzyl)aminomethyl)-3-amino-2-methyl-1,4-benzoxazine dihydrochloride;
6-((2-chlorobenzyl)aminomethyl)-3-amino-2-methyl-1,4-benzoxazine dihydrochloride;
6-((2,4-dichlorobenzyl)aminomethyl)-3-amino-2-methyl-1,4-benzoxazine dihydrochloride;
6-((2,3-dimethylbenzyl)aminomethyl)-3-amino-2-methyl-1,4-benzoxazine dihydrochloride;
6-((3-fluorobenzyl)aminomethyl)-3-amino-2-methyl-1,4-benzoxazine dihydrochloride;
6-((indan-1-yl)-aminomethyl)-3-amino-2-methyl-1,4-benzoxazine dihydrochloride;
6-((indan-2-yl)aminomethyl)-3-amino-2-methyl-1,4-benzoxazine dihydrochloride;
6-((cyclohexylmethyl)aminomethyl)-3-amino-2-methyl-1,4-benzoxazine dihydrochloride;
6-((1,2,3,4-tetrahydronaphth-1-yl)aminomethyl)-3-amino-2-methyl-1,4-benzoxazine dihydrochloride;
6-((3-methoxybenzyl)aminomethyl)-3-amino-2-methyl-1,4-benzoxazine dihydrochloride;
6-((3-nitrobenzyl)aminomethyl)-3-amino-2-methyl-1,4-benzoxazine dihydrochloride;
6-((4-nitrobenzyl)aminomethyl)-3-amino-2-methyl-1,4-benzoxazine dihydrochloride;
6-((4-sulfamoylbenzyl)aminomethyl)-3-amino-2-methyl-1,4-benzoxazine dihydrochloride;
6-((4-methylsulfonylbenzyl)aminomethyl)-3-amino-2-methyl-1,4-benzoxazine dihydrochloride;
6-((4-fluorobenzyl)aminomethyl)-3-amino-2-methyl-1,4-benzoxazine dihydrochloride;
6-((4-dimethylaminobenzyl)aminomethyl)-3-amino-2-methyl-1,4-benzoxazine trihydrochloride; or
6-((2-fluorobenzyl)aminomethyl)-3-amino-2-methyl-1,4-benzoxazine dihydrochloride.

9. A compound of claim 1, which is of the formula Ib wherein $R^6$ is $C_{1-6}$ alkyl and $R^4$ is hydrogen.

10. A compound of claim 9, wherein $R^1$ and $R^2$ together with two adjacent carbon atoms form a 5-, 6-, 7- or 8-membered ring, which is monocyclic or bicyclic, saturated or unsaturated, and which is optionally substituted with —$NR^7R^8$, —$NR^7R^{8'}$ or $C_{1-4}$ alkyl.

11. A pharmaceutical composition which comprises a compound according to claim 1 and one or more pharmaceutically acceptable vehicles or adjuvants.

12. A process for the production of a compound of formula I according to claim 1, which comprises:
reacting a compound of Formula II or its salt

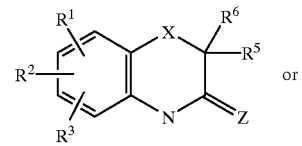

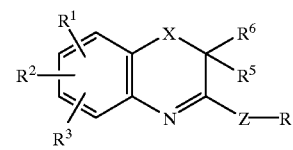

in which
$R^1$, $R^2$, $R^3$, $R^5$, $R^6$ and X have the above-mentioned meaning, Z is oxygen or sulfur and R means $C_{1-6}$ alkyl,
with ammonia or a primary or secondary amine, whereby existing primary and secondary amino groups are optionally intermediately protected and optionally then acylated, optionally isomers are separated and optionally a salt is formed.

13. A compound of the formula IIa

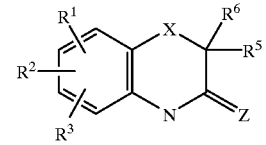

wherein
Z is oxygen or sulfur,
X means O or S,
$R^1$ and $R^2$ together with two adjacent carbon atoms form a 5-, 6-, 7- or 8-membered ring, which is monocyclic or bicyclic, saturated or unsaturated $C_{3-8}$ alkylene radical,
$R^3$ means hydrogen, halogen, —S—$R^9$ or —O—$R^9$ or, independently has one of meanings of $R^1$,
$R^5$ means hydrogen, and
$R^6$ means $C_{3-7}$ cycloalkyl, $C_{6-10}$ aryl, $C_{1-6}$ alkyl, $C_{2-6}$ alkenyl or $C_{2-6}$ alkynyl radicals, which are each optionally substituted with halogen, OH, O—$C_{1-6}$ alkyl, SH, S—$C_{1-6}$ alkyl, $NR^{15}R^{16}$, 5- or 6-membered heteroaryl with 1–3 N, O or S atoms, phenyl or $C_{3-7}$ cycloalkyl.

14. A method for treating a disease induced by the action of nitrogen monoxide at pathological concentrations which comprises administering an NO-synthases inhibiting effective amount of a compound of claim 1.

15. The method of claim 14, wherein the disease is a neurodegenerative, inflammatory, auto-immune or cardiovascular disease.

* * * * *